United States Patent
Varkuti

(10) Patent No.: US 11,246,665 B2
(45) Date of Patent: Feb. 15, 2022

(54) PLANNING OF SURGICAL ANCHOR PLACEMENT LOCATION DATA

(71) Applicant: Brainlab AG, Munich (DE)

(72) Inventor: Balint Varkuti, Munich (DE)

(73) Assignee: BRAINLAB AG, Munich (DE)

( * ) Notice: Subject to any disclaimer, the term of this patent is extended or adjusted under 35 U.S.C. 154(b) by 0 days.

(21) Appl. No.: 17/254,603

(22) PCT Filed: Jul. 23, 2018

(86) PCT No.: PCT/EP2018/069943
§ 371 (c)(1),
(2) Date: Dec. 21, 2020

(87) PCT Pub. No.: WO2020/020433
PCT Pub. Date: Jan. 30, 2020

(65) Prior Publication Data
US 2021/0121236 A1 Apr. 29, 2021

(51) Int. Cl.
*A61B 8/14* (2006.01)
*A61B 34/10* (2016.01)
(Continued)

(52) U.S. Cl.
CPC .............. *A61B 34/10* (2016.02); *A61B 34/20* (2016.02); *A61B 34/25* (2016.02); *A61B 34/30* (2016.02);
(Continued)

(58) Field of Classification Search
CPC combination set(s) only.
See application file for complete search history.

(56) References Cited

U.S. PATENT DOCUMENTS 5,769,789 A 6/1998 Wang et al.
9,439,623 B2 9/2016 Frank et al.
(Continued)

FOREIGN PATENT DOCUMENTS

WO 2006081409 8/2006
WO 2009042130 4/2009
(Continued)

OTHER PUBLICATIONS

Kratchman et al., "Image-Guided Targeting and Control of Implantable Electrodes", Jan. 1, 2015 (Jan. 1, 2015), XP055573076, ISBN: 978-0-355-55633-9. Retrieved from the Internet: URL:https://etd.library.vanderbilt.edu/available/etd-03302015-143838/unrestricted/Kratchman.pdf. 156 pages.
(Continued)

*Primary Examiner* — Joel F Brutus
(74) *Attorney, Agent, or Firm* — Middleton Reutlinger

(57) ABSTRACT

During a sEEG (stereo-electroencephalography) intervention into the skull of a patient, there is requirement to drill a large number of trajectories. Typically, instrument stabilisation platforms and robots for protocols requiring only one or two trajectories are rigidly fixed to the skull using surgical anchor members fixed into the skull around the one or two trajectories. However, because sEEG interventions require a large number of trajectories, an impractical number of surgical anchor members need to be fixed into the skull resulting in patient discomfort. Attachment of an intervention platform to all surgical anchor members is not required at once. Accordingly, it is proposed to search for intersection points of the maximum extent of an intervention platform between at least two trajectory entry points on an object of interest of patient, so that at least one surgical anchor member can be shared when the intersection point is at first and the second trajectories. Any reduction in the number of
(Continued)

surgical anchor members inserted into a patient reduces risk and discomfort. The positioning of the shared anchor members can be optimised to enable good mechanical stability, and/or optical registration performance. Furthermore, the number of surgical anchor members required for intervention can be reduced. Because the surgical anchor members are sterilised and made from high quality metal, a cost for performing the procedure can also be reduced.

12 Claims, 7 Drawing Sheets

(51) Int. Cl.
    *A61B 34/20*     (2016.01)
    *A61B 34/00*     (2016.01)
    *A61B 34/30*     (2016.01)

(52) U.S. Cl.
    CPC ................. *A61B 2034/107* (2016.02); *A61B 2034/2055* (2016.02)

(56) References Cited

U.S. PATENT DOCUMENTS

| | | |
|---|---|---|
| 2009/0177081 A1 | 7/2009 | Joskowicz et al. |
| 2013/0345718 A1* | 12/2013 | Crawford ............. A61B 17/025 606/130 |
| 2013/0346051 A1 | 12/2013 | Gibbs et al. |
| 2014/0066750 A1 | 3/2014 | Piferi et al. |
| 2015/0087965 A1 | 3/2015 | Tokuda et al. |

FOREIGN PATENT DOCUMENTS

| | | |
|---|---|---|
| WO | 2015057807 | 4/2015 |
| WO | 2016205066 | 12/2016 |
| WO | 2017189570 | 11/2017 |
| WO | 2020020433 | 1/2020 |

OTHER PUBLICATIONS

De Momi et al., "Multi-trajectories automatic planner for StereoElectroEncephaloGraphy (SEEG)", International Journal of Computer Assisted Radiology and Surgery, Springer, DE, vol. 9, No. 6, Nov. 1, 2014 (Nov. 1, 2014), pp. 1087-1097, XP009502158, ISSN: 1861-6410, DOI: 10.1007/S11548-014-1004-1.
International Search Report and Written Opinion isssued for Application No. PCT/EP2018/069943 dated Apr. 2, 2019.

* cited by examiner

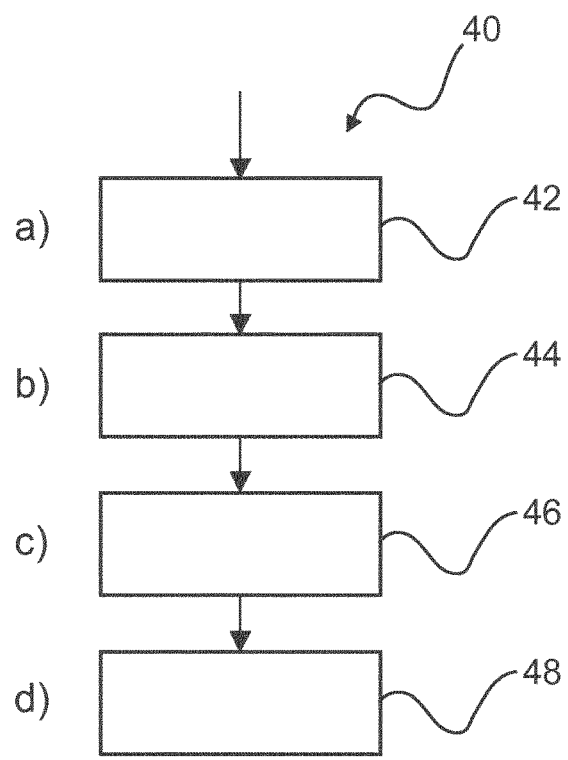
Fig. 2
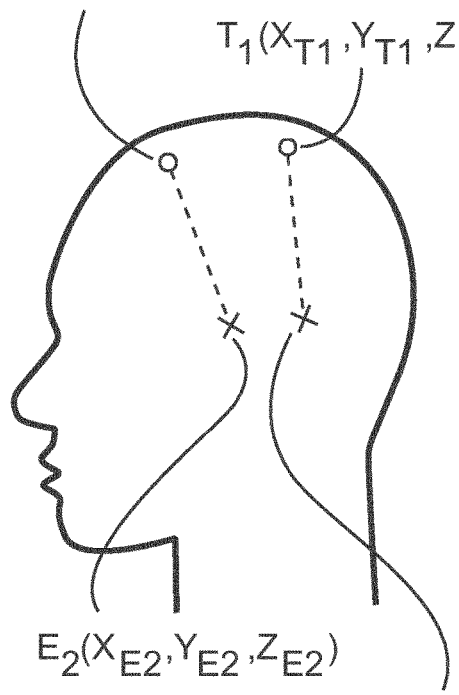
Fig. 3a
Fig. 3b

| T # | Anchor 1 | Anchor 2 | Anchor 3 |
|---|---|---|---|
| 1 | $(X_1, Y_1, Z_1)$ | $(X_5, Y_5, Z_5)$ | $(X_6, Y_6, Z_6)$ |
| 2 | $(X_7, Y_7, Z_7)$ | $(X_8, Y_8, Z_8)$ | $(X_9, Y_9, Z_9)$ |
| 3 | $(X_{10}, Y_{10}, Z_{10})$ | $(X_{11}, Y_{11}, Z_{11})$ | $(X_{12}, Y_{12}, Z_{12})$ |
Fig. 4
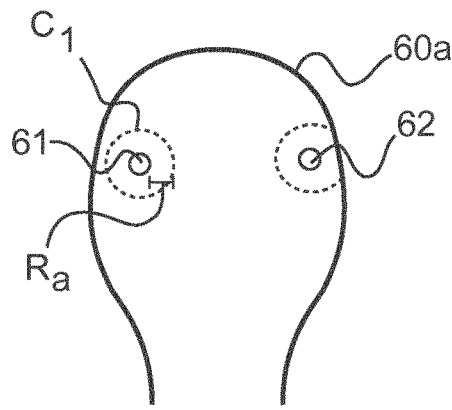
Fig. 5a
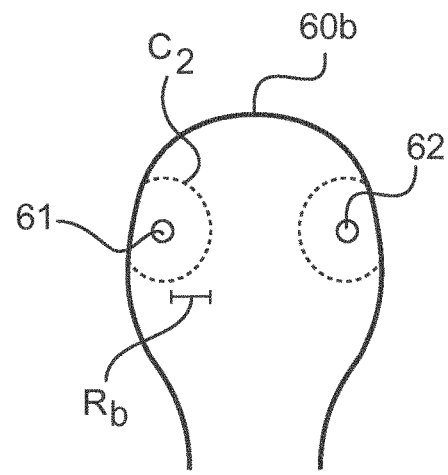
Fig. 5b
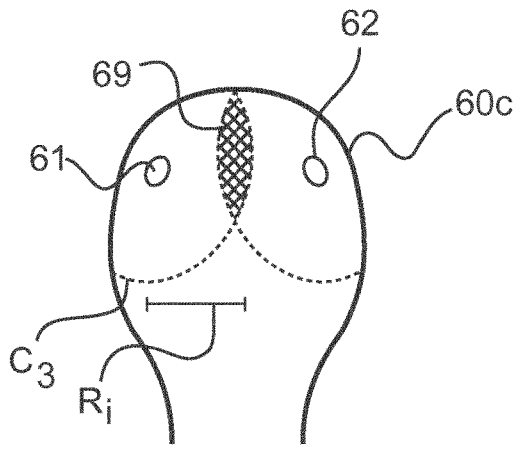
Fig. 5c
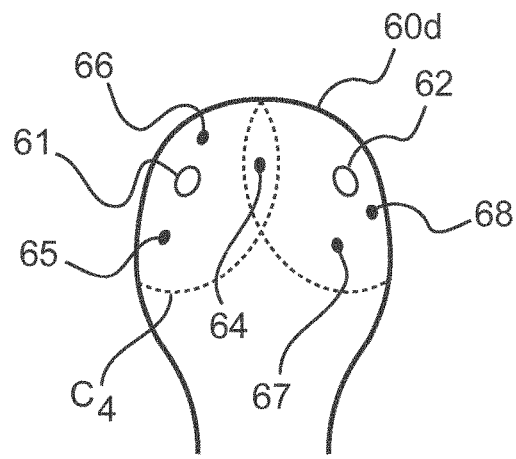
Fig. 5d

PLANNING OF SURGICAL ANCHOR PLACEMENT LOCATION DATA

FIELD OF THE INVENTION

The present invention relates to a computer implemented method for generating placement location data for surgical anchor members, and an associated apparatus, program, client apparatus and server apparatus, client method and server method, system, use, and non-transitory computer-readable program storage medium.

TECHNICAL BACKGROUND

In the field of surgical cranial intervention, there is often a need to place an intervention device inside the cranial cavity of a patient using surgical tools such as electrodes for the purpose of epilepsy treatment, interventions in the regions of the cochleae, or the treatment of cancerous objects inside the skull. For example, stereo-electroencephalography (sEEG) or deep brain stimulation (DBS) require placement of such electrodes along a placement trajectory.

Historically, such surgical cranial interventions have been performed using a "head clamp" fixed directly into the bone of a patient's skull. Such head clamps provide a stable reference mount to a patient that can be used for mounting tool guides and the like during an intervention, and are still widely used. An example of a head clamp (patient support frame) is the "Mayfield frame".

More recently, partially automated cranial intervention procedures have been proposed. In particular, partially automated robotic approaches use a large articulated robot to access the target point, whilst the patient's skull is fixed in a head clamp. Another approach involves the mounting (fixation) of a movable robotic device platform directly onto a patient's skull.

However, improvements to the approaches used in such partially automated cranial intervention procedures are still possible. The present invention has the object of improving the approaches applied to partially automated cranial intervention procedures.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

During a sEEG (stereo-electroencephalography) intervention into the skull of a patient, there is requirement to provide a large number of trajectories. Typically, instrument stabilisation platforms and robots for protocols requiring only one or two trajectories are rigidly fixed to the skull using surgical anchor members fixed into the skull around the one or two trajectories. However, because sEEG interventions require a large number of trajectories, an impractical number of surgical anchor members need to be fixed into the skull resulting in patient discomfort.

Attachment of an interventional platform to all surgical anchor members is not required at once. Accordingly, this application proposes to search for intersection points within the geometric extent of an intervention platform, between at least two trajectory entry points on an object of interest of patient, so that at least one surgical anchor member can be shared when the intersection point is located at first and the subsequent second trajectory. Any reduction in the number of surgical anchor members inserted into a patient reduces risk and discomfort. The positioning of the shared anchor members can be optimised to enable good mechanical stability, and/or optical registration performance. Furthermore, the number of surgical anchor members required for intervention can be reduced without reducing the accuracy of the intervention, since the per-trajectory number of anchors does not decrease. Because the surgical anchor members are sterilised and made from high quality metal, they are expensive. Therefore, the cost for performing the procedure can also be reduced.

In the following, a short description of the specific features of the present invention is given which shall not be understood to limit the invention only to the features or a combination of the features described in this section.

GENERAL DESCRIPTION OF THE INVENTION

In this section, a description of the general features of the present invention is given for example by referring to possible embodiments of the invention.

In general, the invention reaches the aforementioned object by providing, according to a first aspect, a computer implemented method for generating placement location data for surgical anchor members comprising:

acquiring anatomical geometry data comprising a surface geometry of an object of interest;

acquiring surgical plan data comprising at least first and second intervention trajectories into the object of interest relative to the anatomical geometry data;

acquiring geometric constraint data of a repositionable interventional platform for supporting a surgical instrument on the object of interest along the first and second intervention trajectories; and generating placement location data for surgical anchor members comprising a first set of surgical anchor member placement locations for positioning the repositionable interventional platform on the object of interest at a location of the first intervention trajectory, and comprising a second set of surgical anchor member placement locations for positioning the repositionable interventional platform on the object of interest at a location of the second intervention trajectory;

wherein the first and second sets of anchor member locations of the placement location data are generated according to a criterion that at least one shared anchor member location that the repositionable interventional platform is anchored to during a first intervention along the first intervention trajectory and during a second intervention along the second intervention trajectory is present.

Accordingly, the number of anchor points required for the stable fixing of a repositionable interventional platform that need to be invasively placed onto an object of interest (such as a cranium) of a patient when more than one trajectory is required can be automatically reduced, while still enabling an interventional platform significant freedom of movement around an object of interest. This also means that a reduction in the total number of surgical anchors required for an intervention can be realized, saving cost and complexity. Furthermore, an exhaustive search of shared surgical anchor placement possibilities may be performed that would take too long to complete unaided.

According to an embodiment, generating the placement location data further comprises:
- generating a first plurality of candidate surgical anchor member placement locations in a first search region on a surface of the anatomical geometry data centred at the location of the first intervention trajectory;
- wherein the first search region has an extent defined by the geometric constraint data enclosing the location of the first intervention trajectory;
- generating a second plurality of candidate surgical anchor member placement locations in a second search region on a surface of the anatomical geometry data centred at the location of the second intervention trajectory;
- wherein the second search region has an extent defined by the geometric constraint data enclosing the location of the second intervention trajectory;
- generating a final candidate surgical anchor member placement location comprising candidate surgical anchor member placement locations inside an intersecting region of the first and second search regions.

Accordingly, a plurality of shared candidate surgical anchor member placement locations accessible by a repositionable interventional platform in a first and a second position can be automatically identified, to provide more flexibility in the positioning of surgical anchor members.

According to an embodiment, generating the first and second search regions comprises:
- generating a first search region at the location of the first intervention trajectory having a first extent;
- generating a second search region at the location of the first intervention trajectory having a second extent;
- enlarging the first and second extents of the first and second search regions if an intersecting region of the first and second search regions is not found.

Accordingly, potential placement locations for the shared anchor member location that do not require the repositionable interventional platform having a maximum extent may be identified. The search regions may be initialised as having a first, relatively small diameter, which is incrementally enlarged until the first and second search regions touch, or generate an intersection region having a predefined size.

According to an embodiment, generating the first and second search regions comprises:
- enlarging the extent of the first search region at a greater rate than a rate of enlargement the extent of the second search region.

Accordingly, potential placement locations for the shared anchor member location can be biased dependent upon whether or not it is preferred to place the anchor member locations further from the first search region than the second search region. As a non-limiting example, if the first trajectory is located substantially at the top of a patient's head, and the second trajectory is located substantially at the left temple of the patient's head, it will be preferable to enlarge the extent of the search region on the top of the head faster than that at the left temple of the head, to prevent surgical anchor placement locations being proposed near to the ear or the eye sockets, for example.

According to an embodiment, generating the final candidate surgical anchor member placement location inside the intersecting region is performed on the basis of an additional or alternative search criterion.

Accordingly, if owing to the geometric constraint data an intersection region in between the first and second trajectory locations is present, it is possible to define the placement of a shared surgical anchor location within the intersection region according to another goal, for example, the visibility of a surgical anchor to an optical viewing system or the optimisation of the mechanical stability of a repositionable interventional platform in the intersection region.

According to an embodiment, acquiring anatomical constraint data defining regions of an object of interest within which a surgical anchor should not be placed, and generating the first and second search regions comprises:
- generating the first and second search regions on portions of the object of interest that do not intersect with the anatomical constraint data and/or providing first and second sets of anchor member locations that are not within the anatomical constraint data.

Accordingly, portions of an object of interest (such as a human head) can be designated such that surgical anchors are not placed in those regions. This enables a surgical anchor planned to be produced whilst omitting for example the nasal region, the eye socket region, and the ear canal region of the human head.

According to an embodiment, acquiring optical system constraint data defining the position of at least one camera relative to the anatomical geometry data, and wherein generating the first and second search regions comprises:
- generating, for each of the shared candidate surgical anchor member placement locations an optical fidelity measure;
- providing the first and second sets of anchor member locations as locations meeting or exceeding an optical fidelity criterion.

In systems using an optical registration technique to localise, for example, a repositionable interventional platform to a patient in which the optical registration is based upon the expected location of surgical anchors and their relation to an optical reference marker on the repositionable interventional platform, is important that surgical anchors are not aligned at too much of an oblique angle to the camera of the optical registration system. According to this embodiment, shared surgical anchors may be placed to improve the accuracy of an optical registration system.

According to an embodiment, acquiring mechanical stability constraint data of the repositionable interventional platform and wherein generating the first and second search regions comprises:
- generating, for each of the shared candidate surgical anchor member placement locations, a mechanical stability measure;
- providing the first and second sets of anchor member locations as locations meeting or exceeding a mechanical stability criterion.

Accordingly, an example of a repositionable interventional platform comprises legs that may change in one or more degrees of freedom (DOF), such as by telescopic extension, or by tilting away from or towards the object of interest. The less susceptible the repositionable interventional platform is to mechanical disturbance, the greater the accuracy with which a sEEG electrode, for example, may be positioned. Some positions of the planned surgical anchor members will enable a more mechanically stable positioning of the repositionable interventional platform, and this can be an extra factor in the optimisation of the surgical anchor member positioning.

According to an embodiment, there is provided a step of generating fixation orientation data of the object of interest based upon the placement location data. Accordingly, the orientation of the object of interest (such as a patient's head) in a head support frame (for example, a "Mayfield frame") can be chosen to provide more effective alignment with an optical registration system, or more effective mechanical stability when using a repositionable interventional platform.

According to an embodiment, there are provided the steps of:

receiving, via a graphical user interface, a user selection of a preferred candidate surgical anchor member placement location of the shared candidate surgical anchor member placement locations;

generating updated positions of the surgical anchor member placement locations; and displaying, via the graphical user interface, the updated positions of the surgical anchor member placement locations.

Accordingly, external intervention from a user may be used to partially guide the discovery of shared surgical anchor members. For example, a user may specify that a surgical anchor member must be placed in a first preferred location and the computer implemented method then identifies remaining surgical anchor member locations to enable the sharing of at least one surgical anchor between the two trajectories.

According to an embodiment, the placement location data is generated to optimize a reduction in the number of surgical anchor members required to perform an intervention at the first and second trajectories.

Accordingly, the intersection region of first and second search areas may be large enough to make a plurality of candidate surgical anchor member arrangements possible. In this option, it is possible to select the candidate surgical anchor member location resulting in a need for the fewest surgical anchors to be placed into the object of interest.

According to a second aspect, there is provided an apparatus for generating placement location data for surgical anchor members. The apparatus comprises an input unit, a memory unit, and a processing unit.

The input unit is configured to acquire anatomical geometry data comprising a surface geometry of an object of interest, to acquire surgical plan data comprising at least first and second intervention trajectories into the object of interest relative to the anatomical geometry data, and to acquire geometric constraint data of a repositionable interventional platform for supporting a surgical instrument on the object of interest along the first and second intervention trajectories, and to store the anatomical geometry data, the surgical plan data, and the geometric constraint data in the memory unit.

The processing unit is configured to read the anatomical geometry data, the surgical plan data, and the geometric constraint data from the memory unit, and to generate placement location data on the object of interest for surgical anchor members comprising a first set of surgical anchor member placement locations for positioning the repositionable interventional platform at a location of the first intervention trajectory, and comprising a second set of surgical anchor member placement locations for positioning the repositionable interventional platform at a location of the second intervention trajectory.

The first and second sets of anchor member locations of the placement location data are generated according to a criterion that at least one shared anchor member location that the repositionable interventional platform is anchored to during a first intervention along the first intervention trajectory and during a second intervention along the second intervention trajectory is present, and wherein the processing unit is configured to store the placement location data in the memory unit.

According to an embodiment, the apparatus further comprises an output unit. The output unit is configured to read the placement location data from the memory unit, and to display the placement location data to a user.

According to a third aspect, there is provided a program which, when running on a computer or when loaded onto a computer, causes the computer to perform the method according to the first aspect, and/or a program storage medium on which the program is stored;

and/or a computer comprising at least one processor and a memory and/or the program storage medium, wherein the program is running on the computer or loaded into the memory of the computer;

and/or a signal wave or a digital signal wave, carrying information which represents the program;

and/or a data stream which is representative of the program.

In the third aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform the method according to the fourth aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, for example the internet. The invention according to the second aspect therefore may alternatively or additionally relate to a data stream representative of the aforementioned program.

According to a fourth aspect, there is provided a use of placement location data generated according to the program the third aspect, for the surgical treatment of a patient, comprising:

providing at least a first set and a second set of surgical anchor members at surgical anchor member placement locations defined in the placement location data on an object of interest, wherein at least one shared anchor member location that the repositionable interventional platform is anchored to during a first intervention along the first intervention trajectory and during a second intervention along the second intervention trajectory is present;

attaching a repositionable interventional platform to the first set of surgical anchor members;

performing an intervention into the object of interest along a first trajectory using the repositionable interventional platform;

reattaching a repositionable interventional platform from the first set to the second set of surgical anchor members;

performing a second intervention into the object of interest along a second trajectory using the repositionable interventional platform.

According to a fifth aspect, there is provided a client apparatus. The client apparatus comprises an input unit, a memory unit, a processing unit, and a communications unit.

The input unit of the client apparatus is configured to acquire anatomical geometry data comprising a surface geometry of an object of interest, to acquire surgical plan data comprising at least first and second intervention trajectories into the object of interest relative to the anatomical geometry data, and optionally to acquire geometric constraint data of a repositionable interventional platform for supporting a surgical instrument on the object of interest along the first and second intervention trajectories, and to store the anatomical geometry data, the surgical plan data, and the optionally geometric constraint data in the memory unit of the client apparatus.

The processing unit of the client apparatus is configured to read the anatomical geometry data, the surgical plan data, and optionally the geometric constraint data from the memory unit and to transmit it to an external server apparatus via the communications unit of the client apparatus.

The processing unit of the client apparatus is configured to receive from a server apparatus via the communications unit of the client apparatus placement location data for surgical anchor members generated in the server apparatus comprising a first set of surgical anchor member placement locations for positioning the repositionable interventional platform on the object of interest at a location of the first intervention trajectory, and comprising a second set of surgical anchor member placement locations for positioning the repositionable interventional platform on the object of interest at a location of the second intervention trajectory.

According to a sixth aspect, there is provided a server apparatus. The server apparatus comprises an input unit, a memory unit, a processing unit, and a communications unit.

The server apparatus is configured to receive anatomical geometry data, surgical plan data, and optionally geometric constraint data from a client apparatus via the communications unit of the server apparatus, and to store the anatomical geometry data, surgical plan data, and optionally geometric constraint data in the memory unit of the server apparatus.

The processing unit of the server apparatus is configured to load the anatomical geometry data, surgical plan data, and optionally geometric constraint data from the memory unit of the server apparatus, and to generate placement location data for surgical anchor members comprising a first set of surgical anchor member placement locations for positioning the repositionable interventional platform at a location of the first intervention trajectory, and comprising a second set of surgical anchor member placement locations for positioning the repositionable interventional platform at a location of the second intervention trajectory.

The first and second sets of anchor member locations of the placement location data are generated according to a criterion that at least one shared anchor member location that the repositionable interventional platform is anchored to during a first intervention along the first intervention trajectory and during a second intervention along the second intervention trajectory is present. The processing unit of the server apparatus is configured to store the generated placement location data in the memory unit of the server apparatus. The server apparatus is configured to communicate the stored placement location data from the memory unit of the server apparatus to the communications unit of a client apparatus.

According to a seventh aspect, there is provided a computer-implemented client method comprising
acquiring anatomical geometry data comprising a surface geometry of an object of interest,
acquiring surgical plan data comprising at least first and second intervention trajectories into the object of interest relative to the anatomical geometry data, and optionally acquiring geometric constraint data of a repositionable interventional platform for supporting a surgical instrument on the object of interest along the first and second intervention trajectories, and
receiving from a server apparatus placement location data on the object of interest for surgical anchor members generated in the server apparatus.

According to an eighth aspect, there is provided a computer-implemented server method comprising:
receiving anatomical geometry data, surgical plan data, and optionally geometric constraint data from a client apparatus;
generating placement location data for surgical anchor members comprising a first set of surgical anchor member placement locations for positioning the repositionable interventional platform on the object of interest at a location of the first intervention trajectory, and comprising a second set of surgical anchor member placement locations for positioning the repositionable interventional platform at a location of the second intervention trajectory, wherein the first and second sets of anchor member locations of the placement location data are generated according to a criterion that at least one shared anchor member location that the repositionable interventional platform is anchored to during a first intervention along the first intervention trajectory and during a second intervention along the second intervention trajectory is present, and
transmitting the generated placement location data from the server apparatus to the client apparatus.

According to a ninth aspect, there is provided a system comprising a client apparatus according to the fifth aspect, a communications network, and a server apparatus according to the sixth aspect, wherein the client apparatus is configured to acquire anatomical geometry data comprising a surface geometry of an object of interest, acquire surgical plan data comprising at least first and second intervention trajectories into the object of interest relative to the anatomical geometry data, and optionally acquire geometric constraint data of a repositionable interventional platform for supporting a surgical instrument on the object of interest along the first and second intervention trajectories, and to transmit the anatomical geometry data, surgical plan data, and optionally geometric constraint data to the server apparatus over the communications network. The server apparatus is configured to generate placement location data for surgical anchor members, and to transmit the placement location data over the communications network to the client apparatus.

According to a tenth aspect, the invention is directed to a non-transitory computer-readable program storage medium on which the program according to the fifth aspect is stored.

DEFINITIONS

In this section, definitions for specific terminology used in this disclosure are offered which also form part of the present disclosure.

Trajectory

The insertion of an interventional device into a patient follows a trajectory. For example, in electrode stimulation of a brain, an electrode is inserted through a hole in a patient's skull and travels to the treatment region along a trajectory to the treatment location. A trajectory could be followed by a needle, an electrode, or many other surgical interventional devices. In the case of an intervention into the skull, the trajectory is usually a straight line in 3D space beginning at a trajectory entry point typically drilled through the skull, however curved trajectories are also possible.

Path

The term "path" refers to a route that a robotic platform can take between trajectory entry points, ideally with a medical tool support aligned with the path. It will be appreciated that there exist many possible paths between trajectory entry points, which can be calculated as a function of the 3D location of the trajectory entry points, the motion constraints of a robotic platform, and fiducial (attachment anchor) locations on the skull. The path depends on what order it is decided to move between the trajectories.

Repositionable Interventional Platform

A repositionable interventional platform (also referred to as an "articulated robotic platform" in the context of this disclosure) is a mechanical article that is mountable on part of a patient's anatomy (for example, the skull or neurocranium, or the spine). Such repositionable interventional platforms provide a stable support from which to introduce neurological intervention equipment such as sEEG electrodes along their trajectories. In particular, the articulated robotic platform is preferably connectable to fixed support points (fiducial markers) pre-positioned on the patient.

The repositionable interventional platform may also be connectable to an articulated robotic arm using a first joint portion. In use, the articulated robotic arm preferably exerts a stabilising force on the articulated robotic platform. The function of the articulated robotic platform is to provide an accurate and reconfigurable positioning point and support for interventional surgical tools relative to a part of a patient's anatomy, such that the articulated robotic platform can accurately and quickly position and reposition surgical tools along a trajectory inside a part of a patient's anatomy during an intervention.

An repositionable interventional platform may be of a "passive" type comprising support member extension measurement devices, or it may be of an "active" type additionally comprising support member actuators capable of moving the support members of the articulated robotic platform. Optionally, a subset of the support members of the articulated robotic platform may are equipped with actuators.

Large-scale repositioning of the repositionable interventional platform occurs by unattaching support members of the repositionable interventional platform from a first set of support points and attaching them to a second set of support points at a different position on part of the patient's anatomy. In optional embodiments, repositioning of the repositionable interventional platform can also be performed using automatic actuators connected to the support members of the repositionable interventional platform.

The repositioning of the repositionable interventional platform may be unassisted by a medical professional (for example, using controlled actuation of actuators on the platform). The repositioning may be partially or fully assisted by a medical professional. A plurality of support members (legs) are attached to the repositionable interventional platform to support it in close proximity to a part of a patient's anatomy. Preferably, the repositionable interventional platform comprises a rigid support hub (such as a flat, rigid plastic platform). It will be appreciated that many construction techniques can be applied to create the repositionable interventional platform above. For example, the articulated robotic platform may be provided as a rigid, injection-moulded or 3D printed article.

Geometric Constraint Data

The geometric constraint data in the context of this application is a property of the particular repositionable interventional platform type chosen for an intervention. In a simple case, the geometric constraint data is 2D sector defining the maximum extent that the support members of a repositionable interventional platform can reach when deployed on an object of interest. For example, the geometric constraint data may be a pattern defined by the individual extent of each support members of the repositionable interventional platform, such as a composite of three circles each centred on the attachment location of three support member to the repositionable interventional platform. Alternatively, the geometric constraint data may be a toroidal plane defining a location directly underneath the repositionable interventional platform that the support members of the repositionable interventional platform may not access. In other words, the geometric constraint data defines acceptable surgical anchor point locations for supporting the repositionable interventional platform when it is positioned at one trajectory location. The overlap between the geometric constraint data when overlying a first trajectory location, and a second trajectory location, defines a region in which a shared surgical anchor member can be placed. In the case of a rigid interventional platform, the geometric constraint data cannot be configured, however the algorithm herein could still attempt to locate shared surgical anchor mounting points of a fixed interventional platform. It will be appreciated that the geometric constraint data should be mapped to 3D shape data of an object of interest to give an accurate impression of the geometric extent of a repositionable interventional platform (if defined as a 2D pattern). The geometric extent data may vary slightly based upon the morphology of a 3D target object of interest to which the geometric constraint data is mapped. Accordingly, the step of registering the geometric constraint data to anatomical geometry data of a patient at a trajectory entry location before performing a search may be provided, however this is not essential. It follows that different types of repositionable interventional platforms have different geometric constraint data.

Surgical Anchor Member

In the context of this application, the term "surgical anchor member" is, for example, a "fiducial screw" to which a repositionable interventional platform can be rigidly attached during a surgical intervention. For example, in an sEEG intervention, three surgical anchor members may be screwed into a patient's skull around the trajectory entry location, enabling a repositionable interventional platform to be securely attached on top of the surgical anchor members. When two trajectory entry locations are required, it is possible for at least one surgical anchor member to be used (shared) by a repositionable interventional platform when entering both trajectory entry locations, when the geometric constraint data at first and second entry points overlaps.

Anatomical Geometry Data

In the context of this application, the term "anatomical geometry data" refers to data defining physical features of an object of interest, such as patient's skull or spinal region. The "anatomical geometry data" is, for example, a 3D outer surface of the patient derived from CT and/or MRI data. The anatomical geometry data may be registered to a surgical plan, the geometric constraint data, and/or an optical registration system, to enable the accurate registration of a repositionable interventional platform during a surgical intervention.

Anatomical Constraint Data

In the context of this application, the term "anatomical constraint data" defines a spatial portion of the "anatomical geometry data" that should not have a surgical anchor member applied to it. Optionally, the anatomical constraint data may be provided as a binary mask defining areas where a surgical anchor member may, or may not be placed by an automated planning tool. Optionally, the "anatomical constraint data" may be provided as a continuous spatial intensity function (like a contour plot) over the anatomical geometry data to discourage, or to encourage, the placement of surgical anchor members at a specific location. Optionally, the binary mask and continuous spatial intensity function may be combined.

Optical System Constraint Data

In the context of this application, the term "optical system constraint data" defines a range of acceptable surgical anchor member placement locations on a registered object of interest which can be effectively resolved by an optical registration system. For example, the tracking camera of an optical registration system has a substantially cone-shaped visibility characteristic. If surgical anchor members attached to an object of interest are being used for optical registration, and a surgical anchor member is not visible by the tracking camera, or is positioned at a highly oblique angle to the tracking camera, a reduction in optical registration system accuracy can occur. Accordingly, the optical system constraint data defines, for example, a three-dimensional visibility function of the tracking camera of an optical registration system enabling the surgical anchor members to be located within the visibility function.

Optical Fidelity Measure/Criterion

In the context of this application, the term "optical fidelity measure" of a surgical anchor member defines a predicted ratio of deviation between the appearance of a surgical anchor member, or a visible portion of it, when viewed using an optical registration system, compared with the ideal appearance of a surgical anchor member. For example, if a first candidate surgical anchor member location is defined on opposite side of an object of interest to the tracking camera of an optical registration system, and a second candidate surgical anchor member location is defined directly within the viewing cone of the tracking camera, the second surgical anchor member location will be directly visible using the tracking camera, whereas the first surgical anchor member will be more obliquely visible. For example, a cone divergently extending in space from the tracking camera, and the distance of the surgical anchor member from the centre of the cone, is an example of an optical fidelity measure, because the closer the surgical anchor member is to the edge of a cone, the less accurately resolvable it is. This is due to the fact that the closer it is to the edge of the visibility cone, the less perpendicular the angle of a direct line from camera to anchor is. Accordingly, the second candidate surgical anchor member location may enable a higher optical fidelity measure than the first candidate surgical anchor member location.

Mechanical Stability Constraint Data

In the context of this application, the term "mechanical stability constraint data" refers to the degree of stability with which a repositionable interventional platform may be secured to a given configuration of first and/or second sets of anchor member locations. This is a property of the repositionable interventional platform and the placement of the surgical anchor members to which it is mounted and is dependent upon the dimensions and materials of the support members of such a platform, for example. Considering a comparison of a repositionable interventional platform mounted between a first, widely spaced set of anchor member locations, and a second, narrowly spaced set of anchor member locations, the mechanical stability for the first set of anchor member locations will be better than for the second set of anchor member locations. As such, the mechanical stability constraint data of the repositionable interventional platform comprises a function or functions which, for different combinations (extensions, elevations) of leg positions of support members of the repositionable interventional platform, define the tendency of the repositionable interventional platform to move from its intended position in the presence of a deviation force (for example, an sEEG electrode being inserted into a medical instrument support of the repositionable interventional platform). The mechanical stability constraint data could, for example, be provided as a lookup table of experimentally determined values, defining the susceptibility of the repositionable interventional platform to stray from intended position for a number of different support member (leg) configurations in the presence of external forces.

Mechanical Stability Criterion

In the context of this application, the term "mechanical stability criterion" defines a maximum tolerable mechanical stability response in the presence of a deviating force (for example, an sEEG electrode being inserted into a medical instrument support of the repositionable interventional platform). Accordingly, if a large number of candidate anchor member locations is generated, the mechanical stability of the repositionable interventional platform in each of the candidate anchor member locations may be assessed. Candidate anchor member locations leading to an unacceptable degree of instability of the repositionable interventional platform, measured as a 3D deviation in millimetres from an ideal position, for example in response to a deviating force would not satisfy the mechanical stability criterion, and would be removed as candidate anchor member locations.

Fixation Orientation Data

In the context of this application, the term "fixation orientation data" defines the orientation of a head-supporting frame (such as a "Mayfield frame") in relation to the overall system registration of the surgical context (for example, an optical registration).

In view of surgical anchor member placement restrictions caused by mechanical stability, optical visibility of surgical anchor members, and anatomically "forbidden" placement zones such as eye sockets, it may be possible to enlarge number of candidate surgical anchor member placement locations by providing a specific fixation of the object of interest in a head-supporting frame that is defined by the fixation orientation data.

Surgical Plan Data

In the following application, the term "surgical plan data" refers to a data structure geometrically defining at least two desired trajectory entry locations and trajectories into an object of interest. The surgical plan data is, for example, designed by a medical professional to follow a trajectory that causes the least disruption to important parts of the human brain. The surgical plan data is designed using the anatomical geometry data of an individual patent. The surgical plan data may be registered to the anatomical geometry data. For example, simple surgical plan data comprises a definition of the direction of two straight lines in 3D space, along with the starting and stopping point of the lines. When registered to the anatomical geometry data of a patient, the surgical plan data defines the planned intervention trajectories into the patient.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Registering

The n-dimensional image of a body is registered when the spatial location of each point of an actual object within a space, for example a body part in an operating theatre, is assigned an image data point of an image (CT, MR, etc.) stored in a navigation system.

Image Registration

Image registration is the process of transforming different sets of data into one coordinate system. The data can be multiple photographs and/or data from different sensors, different times or different viewpoints. It is used in computer vision, medical imaging and in compiling and analyzing images and data from satellites. Registration is necessary in order to be able to compare or integrate the data obtained from these different measurements.

Marker

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

Imaging Geometry

The information on the imaging geometry preferably comprises information which allows the analysis image (x-ray image) to be calculated, given a known relative position between the imaging geometry analysis apparatus and the analysis object (anatomical body part) to be analysed by x-ray radiation, if the analysis object which is to be analysed is known, wherein "known" means that the spatial geometry (size and shape) of the analysis object is known. This means for example that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is for example defined by the position of the x-ray device, for example by the position of the x-ray source and the x-ray detector and/or for example by the position of the multiplicity (manifold) of x-ray beams which pass through the analysis object and are detected by the x-ray detector. The imaging geometry for example describes the position (i.e. the location and in particular the orientation) and the shape (for example, a conical shape exhibiting a specific angle of inclination) of said multiplicity (manifold). The position can for example be represented by the position of an x-ray beam which passes through the centre of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, for example for all of the points and/or regions of the analysis object. Knowledge of the imaging geometry for example allows the location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made for example to the following publications:
1. "An Efficient and Accurate Camera Calibration Technique for 3D Machine Vision", Roger Y. Tsai, Proceedings of the IEEE Conference on Computer Vision and Pattern Recognition. Miami Beach, Florida, 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344.
3. "Fluoroscopic X-ray Image Processing and Registration for Computer-Aided Orthopedic Surgery", Ziv Yaniv
4. EP 08 156 293.6
5. U.S. 61/054,187

Referencing

Determining the position is referred to as referencing if it implies informing a navigation system of said position in a reference system of the navigation system.

Imaging Methods

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

Fixed (Relative) Position

A fixed position, which is also referred to as fixed relative position, in this document means that two objects which are in a fixed position have a relative position which does not change unless this change is explicitly and intentionally initiated. A fixed position is in particular given if a force or torque above a predetermined threshold has to be applied in order to change the position. This threshold might be 10 N or 10 Nm. In particular, the position of a sensor device remains fixed relative to a target while the target is registered or two targets are moved relative to each other. A fixed position can for example be achieved by rigidly attaching one object to another. The spatial location, which is a part of the position, can in particular be described just by a distance (between two objects) or just by the direction of a vector (which links two objects). The alignment, which is another part of the position, can in particular be described by just the relative angle of orientation (between the two objects).

Medical Workflow

A medical workflow comprises a plurality of workflow steps performed during a medical treatment and/or a medical diagnosis. The workflow steps are typically, but not necessarily performed in a predetermined order. Each workflow step for example means a particular task, which might be a single action or a set of actions. Examples of workflow steps are capturing a medical image, positioning a patient, attaching a marker, performing a resection, moving a joint, placing an implant and the like.

In other words, when having to place a number of trajectories to be used to biopsy, sEEG, or DBS placement utilising head mounted or other arc-less intervention devices (such as cranial landers, robots, or 3D printed systems), usually a minimum number of fiducials have to be placed close to the supposed entry in order to allow maximum mechanical stability of the lander close to the intervention site, as well as to provide good quality registrations in the case of optical navigation. An automated planning tool that reduces the number of necessary surgical anchor points while enhancing reuse of surgical anchor points (such as multiple use of single fiducial's or bone screws). Additionally, avoidance zones (such as muscles or sinuses) can be factored in to help achieve stable, safe, and precise execution of multiple trajectories for both line of sight (optically navigated) as well as robotic arm encoder executed interventions. This reduces the number of surgical anchor points that need to be provided, can optimise the distances between surgical anchor points in view of accuracy requirements, and can provide an improved line of sight for a tracking camera.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein:

FIG. 2 schematically illustrates a computer-implemented method in accordance with the first aspect.

FIG. 3a) schematically illustrates a surgical plan with reference to a patient.

FIG. 3b) schematically illustrates a data structure for storing a surgical plan.

FIG. 4 schematically illustrates an example of a computer data format of placement location data.

FIGS. 5a) to 5d) schematically illustrates a spherical search algorithm for surgical anchor location placement discovery.

DESCRIPTION OF EMBODIMENTS

Intra-cranial interventions often involve the insertion of a needle or other surgical implement into the cranial cavity (and through the brain tissue) along trajectories that have been pre-planned. To support the movement of the needle into the cranium, a surgical tool support is physically secured to the cranium at surgical anchor attachment points that are drilled into the surface of the skull. The needle can then be accurately advanced along its pre-planned trajectory to perform a medical operation. However, cranial interventions such as for deep brain stimulation (DBS) or stereo-electroencephalography (sEEG) do not require one trajectory, but a plurality, and often ten or more.

Providing surgical anchor attachment points is inherently invasive. Some surgical tool supports require three or four surgical anchor attachment points per trajectory entry location. Using such supports with an sEEG intervention having fourteen trajectories would imply the drilling of at least forty two surgical anchor attachment holes, as well as the fourteen trajectory holes. This number is unacceptable in terms of the physical discomfort and potential for infection that a patient would be exposed to. However, there is an opportunity to rationalize the number of surgical anchor attachment points used, because a surgical tool support is typically only located at one trajectory location at each time instant, and is successively removed and reattached to successive surgical anchor attachment points according to a surgical plan. Other types of surgical tool support are based on complex, 3D printed frames designed to be specific to an individual patient. These require surgical anchor supports to be present at the time of generating image data with which the 3D printed frame is designed, and the surgical anchor supports must remain in place for the several days required to procure the 3D printed frame, causing discomfort and, potentially, inaccuracy if the pre-placed anchor supports move in the duration between taking measurements and receiving the 3D printed frame. Therefore, the reduction of the number of surgical anchor attachment points whilst maintaining sub-millimetre accuracy is a complex problem, owing to the large number of variables (for example, the complexity of the patient's head shape, the mechanical extent of the surgical tool support, the order of steps required in the intervention).

Figure 1A:
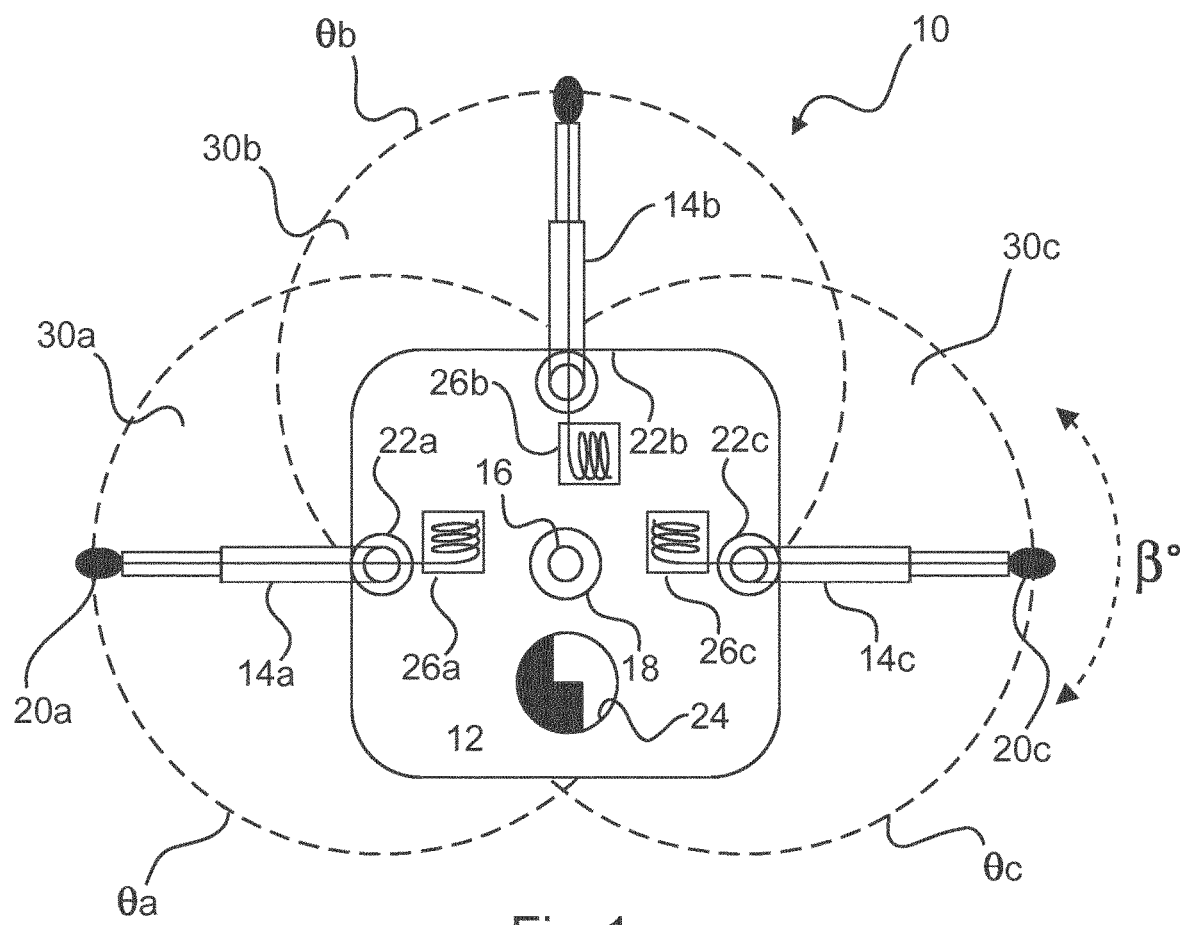
FIG. 1a) schematically illustrates a plan-view of a repositionable interventional platform.

FIG. 1a) schematically illustrates a plan view of an example of an articulated robotic platform 10 that can be used as a surgical tool support. It comprises a base member 12 functioning to support a plurality of support members 14a, 14b, 14c. The base member 12 may, for example, be fabricated from a rigid polycarbonate sheet and optionally have a radiopaque property, although many other materials may be used. Surgical anchor member locations for use with the repositionable interventional platform may be automatically planned to support the articulated robotic platform 10. The articulated robotic platform 10 described is only one possible surgical tool support, and it will be appreciated that many variations are possible.

An aperture 16 is provided through the centre of the base member 12 (although the aperture could be at any other position of the base member 12). A medical tool support 18 is (integrally or removably) provided through the aperture 16. For example, the medical tool support 18 may be an integral portion of the polycarbonate base member 12. Alternatively, the medical tool support 18 is be provided in a threaded or "interference fit" relationship with the base member 12. The medical tool support 18 functions to allow a medical professional to accurately guide a surgical instrument (such as an sEEG electrode) along an intervention trajectory during treatment of a patient. For example, the medical tool support 18 can provide support for an electrotherapy electrode to be positioned in a position within the cranium when treating epilepsy patients. It will be appreciated that medical tool supports 18 of many different forms can be provided (for example, drill guides, electrode guides) to enable medical tools to be accurately positioned during treatment.

A spatial relationship between medical tool support 18 and the intervention region of a patient is defined by the distance and inclination of the base member 12 from the intervention region of the patient. Accordingly, a plurality of support members 14a, 14b, 14c are attached to the base member 12 (in the illustrated case, three, although the skilled person will appreciate that two or four, five, six, seven, eight, or greater than eight support members may be provided).

Figure 1B:
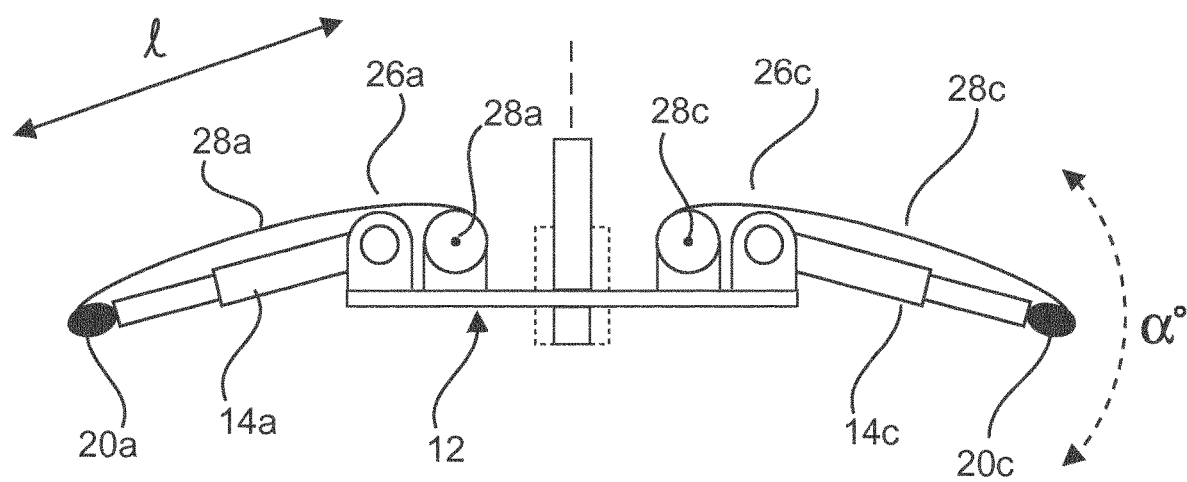
FIG. 1b) schematically illustrates a side projection of a repositionable interventional platform.

FIG. 1b) schematically illustrates a side projection of the articulated robotic platform 10 (repositionable interventional platform).

In the exemplary articulated robotic platform 10 illustrated in FIGS. 1a) and 1b), the distal ends of each of the plurality of support members are provided with distal ends 20a, 20b, and 20c configured to be connectable to a plurality of surgical anchor members. The surgical anchor members are anchored in a patient's cranium prior to the beginning of interventional treatment, according to the placement data generated according to the first aspect described herein.

In the illustrated example, the articulated robotic platform 10 comprises mobile support members 14a, 14b, 14c that are attached to the base member 12 at the proximal ends of the support members by articulated connections 22a, 22b, 22c.

The articulated connections 22a, 22b, 22c are, for example, provided as one of the general types of articulated joint alone or in combination such as a prismatic joint, a revolute joint, a helical joint, a cylindrical joint, a spherical joint, a planar joint, or combinations of these. In case of a prismatic joint (the hinge) the support member can move with one degree of freedom (DOF), whereas a more conjugated joint such as a spherical joint enables the support member to move with three DOF.

The exemplary articulated robotic platform 10 illustrated in FIGS. 1a) and 1b) comprises spherical joints as articulated connections 22a, 22b, 22c enabling each of the support members 14a, 14b, and 14c to move with three DOF. Accordingly, each support member 14a, 14b, and 14c can move along an arc $\beta$ degrees in an azimuth plane (coplanar with the base member 12) and along an arc $\alpha$ degrees in an inclination plane (normal to the azimuth plane).

A first joint portion 24 fixed to the base member 12 enables the articulated robotic platform 10 to be rigidly attached to a motion effector such as an articulated robotic arm. The fact that the first joint portion 24 is rigid means that a force applied to the first joint portion 24 of the articulated robotic platform 10 by an articulated robotic arm (not shown in FIGS. 1a) and b)) will be directly transmitted to the articulated robotic platform 10. The first joint portion 24 is optionally formed have an improved torque handling capability. For example, the first joint portion 24 is provided as a polycarbonate cylinder with a crenelated outer pattern to match a crenelated outer pattern of a second joint portion on a distal end of an articulated robotic arm to which the articulated robotic platform can be attached 10. Optionally, the joint portion 24 may carry an electrical connector to carry data communications between the articulated robotic platform 10 and a controller via an articulated robotic arm.

The support members 14a, 14b, and 14c illustrated in FIGS. 1a) and 1b) are configured to have a variable length (extension). In the illustrated example, they comprise two concentrically arranged telescopic members in slidable relationship capable of changing their total length of extension I, however many other mechanisms enabling a variable-length support member could be used.

Optionally, in a passive version of the articulated robotic platform 10 with no powered actuators, the telescopic support members 14a, 14b, and 14c change their length as the articulated robotic platform 10 is pulled in three-dimensions by an articulated robotic arm. Optionally, in an "active" version of the articulated robotic platform having actuated support members 14a, 14b, 14c, actuators (not shown) actively change their length using the actuators.

The illustrated exemplary embodiment of the articulated robotic platform comprises extension measurement sensors 26a, 26b, 26c enabling the feedback of support member linear extension data to a controller (optionally via an electrical data connection through the first joint portion 24, or optionally via a short-range wireless data connection). In the illustration, the linear extension is measured using a taut measurement cord 28a wrapped around a sprung drum 28b. With this type of linear extension sensor, a support member 14a in its shortest (retracted) position implies that the measurement cord 28a will be fully wrapped around the sprung drum 28b (excepting the length of measurement cord required to pass from the sprung drum 28 to the end of the retracted support member 14a). Whether by passive action (applied by a force from a articulated robotic arm) or by active action (generated by actuators on the articulated robotic platform 10 the movement of base member 12 causes a lengthening of support member 14a, for example. The measurement cord 28a is thus gradually deployed from the sprung drum 28b. The sprung drum 28b may comprise, for example, a rotary encoder enabling the generation of extension measurement data of the support member 14a during his extension. The extension measurement data 14a may be transmitted via an electrical connection in the first joint portion (or via a short-range wireless network) to a controller.

It will be appreciated that the illustrated and described example of an extension measurement sensor based upon a sprung drum 28b holding a taut cord 28a is one example, and alternatively the support members 14a, 14b, 14c of the articulated robotic platform 10 are provided with linear encoders or other extension measurement devices.

In a variation, the distal ends 20a, 20b, 20c of the support members 14a, 14b, and 14c are provided with distal ends configured to be capable of detecting the identity of an anchor member that they are attached to, or are about to be attached to, and are furthermore capable of transmitting this information to a controller via the first joint portion 24 or a short-range wireless connection. The identity of an anchor member may be detected, for example, by using anchor members having RFID tags, and by providing RFID readers on the distal ends 20a, 20b, 20c of the support members 14a, 14b, and 14c. Accordingly, the articulated robotic platform is optionally capable of detecting additional position information provided to the RFID-enabled fiducial markers have a known position on an interventional region of a patient.

Optionally, one or more of the distal ends 20a, 20b, 20c may be attached to a surgical anchor member using, for example, a screw connection or a "snap connection" using high-strength magnets (such as neodymium magnets).

The articulated robotic platform 10 has support members 14a, 14b, and 14c that can move in several degrees of freedom (independently changing their elevation, extension, and pan). Accordingly, the articulated robotic platform 10 has an associated geometric constraint region illustrated in FIG. 1a) as the three circle segments 8a, 8b, $\theta_c$, with each having a minimum and maximum radius defined by the minimum and maximum extension of the respective support members 14a, 14b, and 14c. Any location in segment $\theta_a$ is reachable by support member 14a, any location in segment $\theta_b$ is reachable by support member 14b, and any location in segment $\theta_c$ is reachable by segment 14c—assuming the proviso that one support member is not trespassing into the segment of an adjacent support member.

The geometric constraint is unique to a given design of repositionable interventional platform. Of course, the geometric constraint will be modified slightly dependent on the physical shape that the repositionable interventional platform is positioned on. Thus, the geometric constraint of the repositionable interventional platform may be registered to anatomical geometry data of a particular patient at a particular trajectory entry location to improve the accuracy of the geometric constraint.

In the specific example of the repositionable interventional platform of FIG. 1a), the combined design-space of possibilities for the locations of the distal ends 20a, 20b, 20c of the support members 14a, 14b, and 14c is defined by the mechanical design of the support members 14a, 14b, and 14c, and the overall orientation of the articulated robotic platform itself. This design space may be used to generate geometric constraint data of the repositionable interventional platform. When combined with a trajectory location (in surgical plan data) and patient anatomy information (in anatomical geometry data), the geometric constraint data is may be used to search for an appropriate configuration of surgical anchor member locations around a first trajectory. Accordingly, the geometric constraint data optionally comprises a plurality of geometric constraint configurations of a repositionable interventional platform. This is only an example, and a less complicated robotic platform (or even a passive surgical tool support with no movable support members) will have a less complicated design-space of possibilities. Of course, if the support members 14a, 14b, and 14c could be configured to reach underneath the base member 12, that would enable a more complex geometric constraint that is wider than illustrated in FIG. 1a). Furthermore, a passive surgical tool support without movable legs may only have a design space involving three static distal ends 20a, 20b, 20c directly on the platform that cannot be extended, for example (such as a conventional intracranial landing robot). In this case, the design space simply comprises a circular line or arc section at a fixed distance from the trajectory entry point.

The generation of a set of anchor member locations appropriate for placing the surgical anchor members for a repositionable interventional platform is, thus, dependent on the geometric constraint data of the repositionable interventional platform. In addition, the set of anchor member locations is also dependent upon the anatomical geometry data of a patient defined by, for example, pre-operatively obtained CT and/or MRI scans. Finally, the set of anchor member locations is also dependent on a specific surgical plan defined pre-operatively by a medical professional. The surgical plan is captured in surgical plan data, and defines the location of trajectories at the object of interest (for example, the skull) of a patient. Typically, the trajectories are defined with reference to, and registered to, the pre-operatively obtained anatomical geometry data. Optionally, the surgical plan data is hierarchical (in other words, it requires the repositionable surgical platform to be moved between trajectory locations in a specific order). Optionally, the surgical plan data is freely-planned (in other words, there is no restriction for the repositionable surgical platform to be moved between trajectory locations in a specific order).

Optionally, more accurate geometric constraint data may be generated if the original geometric constraint data of a repositionable interventional platform is registered to the anatomical geometry data at each trajectory entry location before the search process.

Accordingly, there is provided a computer-implemented method in accordance with the first aspect.

FIG. 2 schematically illustrates the method.

The method comprises: a computer implemented method 40 for generating placement location data for surgical anchor members comprising:

acquiring 42 anatomical geometry data comprising a surface geometry of an object of interest;

acquiring 44 surgical plan data comprising at least first and second intervention trajectories into the object of interest relative to the anatomical geometry data;

acquiring 46 geometric constraint data of a repositionable interventional platform for supporting a surgical instrument on the object of interest along the first and second intervention trajectories; and generating 48 placement location data for surgical anchor members comprising a first set of surgical anchor member placement locations for positioning the repositionable interventional platform on the object of interest at a location of the first intervention trajectory, and comprising a second set of surgical anchor member placement locations for positioning the repositionable interventional platform on the object of interest at a location of the second intervention trajectory;

wherein the first and second sets of anchor member locations of the placement location data are generated according to a criterion that at least one shared anchor member location that the repositionable interventional platform is anchored to during a first intervention along the first intervention trajectory and during a second intervention along the second intervention trajectory is present.

Acquiring 42 anatomical geometry data involves acquiring data describing the anatomical detail of an object of interest specific patient, and in the present case may be, for example, data derived from a CT scan, an MRI scan, a PET scan, a MEG scan, or combinations of these, in file data formats known to the skilled person. Of course, other sources of anatomical data may be used. The data may be obtained directly from a pre-operative patient scan, or from a hospital PACS system, for example. The anatomical geometry data at least defines the external surface of an object of interest of a patient (such as a skull) to an accuracy of millimetres or fractions of a millimetre.

Acquiring 44 surgical plan data is, in a basic form, obtaining the locations (coordinates in 3D space registered to the anatomical geometry data) of a plurality of interventional trajectories beginning from the surface of the object of interest and ending at a position inside the object of interest defined by a surgeon. FIG. 3a) schematically illustrates an object of interest 50 in which a surgeon has planned to insert trajectory $T_1$ from coordinate ($x_{T1}$, $y_{T1}$, $z_{T1}$) to ($x_{E1}$, $y_{E1}$, $z_{E1}$), and trajectory $T_2$ from coordinate ($x_{T2}$, $y_{T2}$, $z_{T2}$) to ($x_{E2}$, $y_{E2}$, $z_{E2}$). Optionally, the surgical plan data is generated using planning system software based on a Graphical User Interface (GUI) placement of trajectories in the anatomical geometry data. Accordingly, the surgical plan data 52 comprises a data record enumerating each trajectory, and its start and stop coordinates. Of course, in a simpler case the surgical plan data may simply comprise the locations of entry into the object of interest (in this case, ($x_{T1}$, $y_{T1}$, $z_{T1}$) and ($x_{T2}$, $y_{T2}$, $z_{T2}$)). However, surgical plan data comprising the full trajectory enables the entry angle of a repositionable interventional platform to be defined. Optionally, the surgical plan data can be provided with a hierarchy requirement defining the order in which trajectories $T_1$, $T_2$ are visited by the repositionable interventional platform 10. Although for clarity FIG. 3a) illustrates two trajectories, it will be appreciated that substantially more trajectories would be present in a typical sEEG intervention.

Optionally, the surgical plan data comprises a surgical anchor requirement field for each trajectory, defining how many surgical anchor points need to be provided for a repositionable interventional platform at each trajectory $T_1$, $T_2$. Typically this number will be constant, but in cases where more stability is required, one support member 14a of the repositionable interventional platform may be attached to a head support frame, requiring one fewer surgical anchor holes at the object of interest, for example. Although FIGS. 2a) and b) illustrates two trajectories are illustrated, it will be appreciated that a large plurality of trajectories may be defined in the surgical plan data.

Acquiring 46 geometric constraint data of a repositionable interventional platform comprises acquiring a function, look-up table, or model defining the possible range configurations of the support members 14a, 14b, 14c of a repositionable interventional device chosen for use by a medical professional, as discussed above in relation to articulated robotic platform 10 and regions $\theta_a$, $\theta_b$, and $\theta_c$. The geometric constraint data is registered to a common coordinate system shared by the anatomical geometry data and the surgical plan data. Optionally, the geometric constraint data of the repositionable interventional platform is registered to the anatomical geometry data when centred on each trajectory entry point.

The process of generating 48 placement location data 54 for the surgical anchor members is a search process. An initial estimate of the total number of surgical anchor member locations required in a conventional situation is optionally generated. For example, in a scenario using the articulated robotic platform 10 illustrated in FIG. 1 at three trajectory entry locations, a total of 9 surgical anchor member locations would conventionally be provided. Through the application of an anchor member reduction (optimization) process to be described subsequently, it is possible to discover areas where, when the repositionable surgical platform is repositioned between the trajectories, at least one surgical anchor member location may be shared between two trajectories (either by supporting the same support member 14a, or a different one). Such an outcome is shown in FIG. 4, which illustrates placement location data 54a generated for three trajectories, each requiring the repositionable interventional platform to use three surgical anchor member locations. In this example, trajectories #1 and #2 require entirely unique surgical anchor member locations.

However, the search algorithm has determined that, owing to the geometric constraint possibilities of the repositionable interventional platform, trajectory #2 may share its anchor 3 location ($x_9$, $y_9$, $z_9$) with trajectory #3's anchor 2 location ($x_{11}$, $y_{11}$, $z_{11}$), indicated in the placement location data 54a by locus 56. This enables a reduction in the number of surgical anchor members inserted into an object of interest (a patient's skull) of one, which reduces discomfort appreciably. Optionally, the search algorithm may determine a plurality of placement location data 54a options 54a, 54b, 54c, 54d. Optionally, the plurality of placement location data options 54a, 54b, 54c, 54d are provided for different configurations of the geometric constraint data of the repositionable interventional platform 10. Optionally, the plurality of placement location data options 54a, 54b, 54c, 54d are ranked according to the total number of surgical anchor member placement locations saved, compared to the conventional case. Optionally, the placement location data option enabling the greatest saving in surgical anchor member locations is chosen as the placement location data.

Once the placement location data 54a has been generated, it is used by a medical professional to plan, and to implement the positioning of the surgical anchor member placement locations in the object of interest of the patient (such as the patient's skull).

Table 1 demonstrates a pseudocode representation of an example of a search algorithm that can find a shared surgical anchor locations. This example of a search algorithm seeds a first search sphere at the location of first trajectory a, and a second search sphere and the location of second trajectory b, with the centre of the spheres being located at the location of the trajectories (surgical plan data) on the surface data (anatomical geometry data) of the object of interest. The maximum radius (extent) of the spherical search from the two trajectories is defined by the maximum leg length based on of the properties of the intervention device (geometric constraint data).

TABLE 1

Pseudocode representation of one example of a surgical anchor member search algorithm.

%load base image and trajectory plan:
%load geometric properties of the intervention device
%for example – contains maximum leg extent
% check for each possible combination of trajectory
% pairs whether a common anchor is present:
[3] for a=1:max(length(trajectories))
SURF = calculate skin_surface (Trajectory_Plan(image));
sphere.possible.anchors.maxradius =
Interventiondevice.properties_max_leg_length;
%iterate through the adjacency matrix of all possible trajectory
%combinations to find common anchors:
For b = a + 1:max(length(trajectories))
Common_anchors(a,b) = calculate_intersection
(sphere_possible_anchors(a), sphere_possible_anchors(b), SURF);
END TABLE 1-continued Pseudocode representation of one example of
a surgical anchor member search algorithm.

```
%if for a trajectory, no common anchors can be placed, place these
freely
If isempty(Common_anchors(a,:)) = 0;
Display("place anchors for "a" independently)
```

Therefore, surgical anchor placement points of the intervention device in respect of intersections of the first and second search spheres on the surface of the anatomical geometry data provide common surgical anchor locations of a repositionable interventional device in respect of the first and second trajectory entry locations. The geometrical extent data defines a maximum search extent of the first and second search spheres. Any plurality of trajectories may be investigated in this way. Although the pseudocode uses a spherical search algorithm on the surface of the anatomical geometry data, many search algorithms are applicable for reducing the number of shared surgical anchors. In this case, the extent of the search algorithm is defined by the maximum length of the leg of the repositionable interventional device. As discussed above, this is only one option and the geometric constraint data may take the form of a more complex shape, many other shapes, in which case other shapes of expanding manifold may be used in search algorithm (as opposed to a sphere). Additionally, the geometric constraint data may be a complex function based upon the configuration of one or more support members of the repositionable interventional device. Optionally, the search algorithm is iterated through the different configurations of the geometric constraint data.

Optionally, the first and/or second pluralities of candidate surgical anchor member placement locations may be placed according to a standard (or starting) configuration of the repositionable interventional device relative to the trajectory entry points. Optionally, the first and/or second pluralities of candidate surgical anchor member placement locations may be randomly seeded within the definition of the geometric constraint data of the repositionable interventional platform positioned, respectively, relative to the first and/or second trajectory entry points.

FIG. 5 schematically illustrates the spherical search algorithm throughout several stages. In FIG. 5a, a first 61 and second 62 trajectory entry point have been defined on the anatomical geometry data 60a. A first search sphere having a radius $R_A$ represented by its contour $C_1$ on the anatomical geometry data 60a surrounds the first trajectory entry point 61. The dotted line on the surface of the head in FIGS. 5a) to 5d) represents the intersection point of the sphere centred on the trajectory entry location used in the search with the anatomy, for clarity. In FIG. 5b), the first and second search spheres have expanded to an extent $C_2$, although with no intersection. In FIG. 4c), the first and second search spheres have expanded such that they each have an extent $C_3$. Accordingly, intersection region 69 is present inbetween the first 61 and second 62 trajectory entry points. This represents a region where a repositionable interventional lander may land at trajectory entry points 61 or 62, and share a surgical anchor if it is positioned in the intersection region 69. Accordingly, in FIG. 5d), there is an illustration of surgical anchor member locations 65 and 66 used by a repositionable interventional platform when positioned at trajectory 61, and surgical anchor member locations 67 and 68 used by a repositionable interventional platform when positioned at trajectory 62. Surgical anchor member location 64 is used by the repositionable interventional platform when positioned over both of the trajectories and is thus a shared anchor member location. Anchor member locations 66, 65, and 64 are an example of candidate surgical anchor member placement locations in a first search region. Anchor member locations 68, 67 and 64 are an example of candidate surgical anchor member placement locations in a second search region. Anchor member 64 is an example of a candidate surgical anchor member at an intersecting region of first and second search regions.

Optionally, the search algorithm initially identifies a location for one or more shared anchor member points, and then places the non-shared anchor member fixation points dependent on the location of the respective one or more shared anchor member points.

Optionally, the first search region may be enlarged at a greater rate than the rate of enlargement of the second search region. Advantageously, when the second trajectory is placed nearer to a sensitive structure (for example, sinus) this enables placement of candidate surgical anchor member placement locations to be biased towards the first search region. Optionally, the second search region may be biased away from a sensitive structure (centred at an offset from the second trajectory location).

The use of an optical fidelity measure and a mechanical stability measure are discussed subsequently. However, if for the positioning of the repositionable interventional platform at a particular trajectory entry point, the optical fidelity measure and/or the mechanical stability measure are likely not to satisfy a first criterion, the search algorithm causes the search region at this trajectory entry location to expand at a slower rate than for a search region centred on a trajectory entry location benefiting from good optical and/or mechanical stability. In this way, shared surgical anchor fixation points are likely to be biased away from placement areas resulting in a lower optical fidelity and/or mechanical stability.

Optionally, the method may use an alternative approach for placing a shared surgical anchor member inside the intersecting region 69 of the first and second search regions. For example, once the maximum extent of the first search region and the second search region have revealed an intersecting region 69 of the first and second search regions, placement of a shared anchor member within the intersecting region 69 may be determined based upon additional geometric constraint data of the repositionable interventional platform (for example, the position of the shared surgical anchor member inside the intersecting region 69 may ensure that the repositionable interventional platform has an optimal stability when positioned over the first and second trajectory entry locations).

Although the search algorithm has been discussed in terms of spheres intersecting on the surface of the anatomical geometry data, it will be appreciated that many search approaches could enable the discovery of shared surgical anchor member placement locations given a starting point of anatomical geometry data, surgical plan data, and geometric constraint data of a repositionable interventional platform. For example, a genetic algorithm applied on the surface of the anatomical geometry data (such as a multiple objective evolutionary algorithm), or a 2D circle packing algorithm, could be used.

Optionally, the shape of the first and/or second search regions is based on the geometric constraint data of the repositionable platform.

Figure 6:
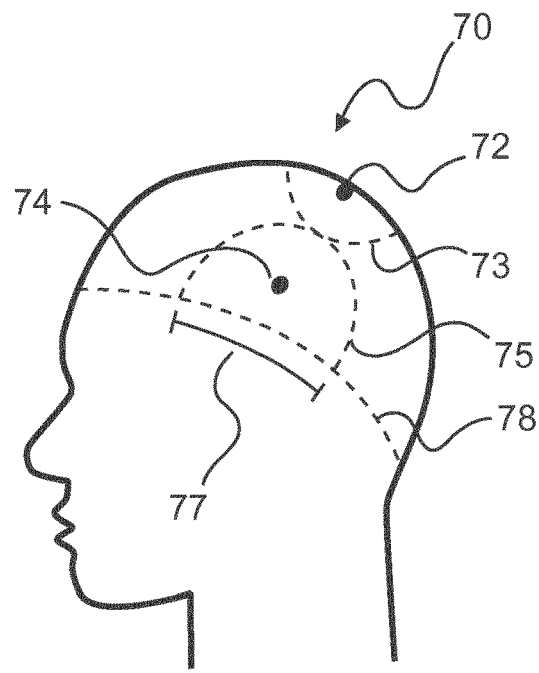
FIG. 6 schematically illustrates a 2D side view of anatomical constraint data.

Optionally, the search algorithm may also be constrained so that it does not propose the placement of surgical anchors on unsuitable parts of the anatomy. For example, FIG. 6 illustrates a visualisation of anatomical geometry data 70 of a patient in a 2D schematic side view of a patient 70, where the surgical plan data defines trajectory entry locations at locations on the anatomical geometry data at 72 and 74. A first contour 73 illustrates the intersection of the first spherical search region 73 with the anatomical geometry data. A second contour 75 illustrates the intersection of the second spherical search region with the anatomical geometry data. In this case, anatomical constraint data is defined as the line 78 crossing the head of the patient between the forehead and the back of the head. The anatomical constraint data defines that in a region of the head underneath the line 78, surgical anchor locations should not be placed. Accordingly, a boundary 77 between the second spherical search region defined by contour 75 and the anatomically constrained location exists preventing the further expansion of the second spherical search region. In practice, this means that even though a repositionable interventional platform could reach into the region defined by the anatomical constraint data, surgical anchor members will not be proposed for placement in the anatomical constraint data region. This prevents surgical anchor members being placed where they would cause permanent anatomical damage or cosmetic disfigurement, for example. Optionally, the anatomical constraint data is provided as a binary map registered to the anatomical geometry data. Optionally, the anatomical constraint data is provided as a "soft" function registered to the anatomical geometry data. For example, the anatomical constraint data is provided on a scale of 1 to 5, where a region having the value 1 means that a surgical anchor certainly should not be placed, and a region having a value 5 means that a surgical anchor may be placed if no other alternative can be found. This enables the search algorithm to be discouraged from placing surgical anchor locations too close to sensitive parts of the patient's anatomy, but ensures that the search algorithm does not become ill-conditioned in a case that finding suitable surgical anchor locations is difficult.

Figure 7:
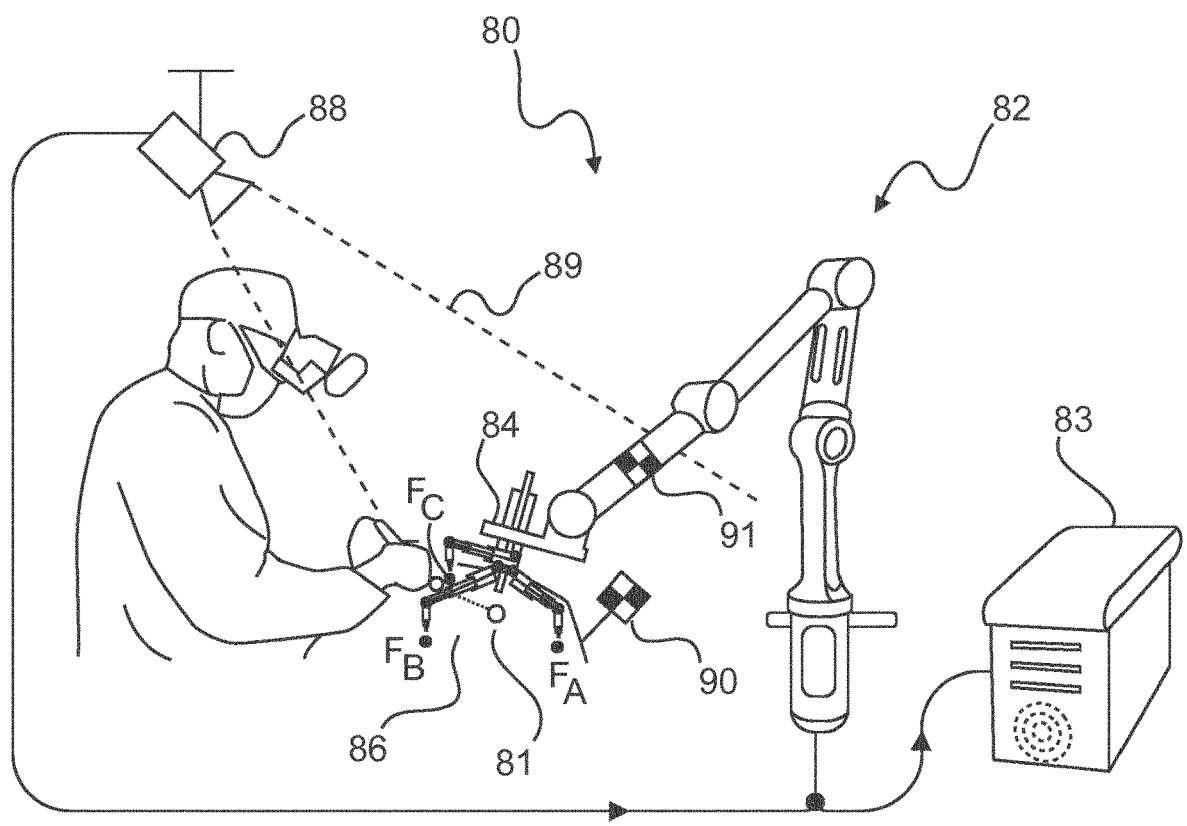
FIG. 7 schematically illustrates an interventional system.

FIG. 7 illustrates an example of an interventional system 80 comprising a robotic arm 82 configured to removably support a repositionable interventional platform 84 at an intervention region of a patient 86. The robotic arm 82 holds the repositionable interventional platform 84 in a highly accurate (to sub-millimetre accuracy) stable equilibrium over a first trajectory entry location 81 of the patient. Feedback signals from the repositionable interventional platform 84 and the robotic arm 82 are transmitted to the control system 83. The trajectory entry locations and surgical anchor locations $F_A$ and $F_B$ in FIG. 6 have been calculated according to the computer-implement method according to the first aspect, for example.

The interventional system 80 further comprises a camera 88 configured obtain a visual representation of the repositionable interventional platform 84, the object of interest of the patient 86, and optionally the robotic arm 82. The camera 88 transmits the visual representation to the control system 83. The signal from the camera 88 is used by the control system 83 to provide optical registration of the repositionable interventional platform 84 with respect to the intervention region of the patient 86. Ideally, the camera 88 is positioned such that a viewing cone 89 can effectively capture optical reference markers (for example marker 90—attached to the patient, and 91 attached to the robotic arm, or to the interventional platform (not shown)).

Surgical anchor members have a dual use, because they can be used as supports for a repositionable interventional platform. However, when not in use for securing a repositionable interventional platform, surgical anchor members also provide registration points for an optical registration algorithm. Accordingly, according to an embodiment, the first and second sets of surgical anchor member locations may be planned to exceed an optical fidelity criterion when not in use by the repositionable interventional platform. Optical system constraint data defining the geometric location and optical characteristics of a camera in an interventional system relative to a patient (and their associated anatomical geometry data) is provided. For example, the optical fidelity criterion may be a geometric accuracy threshold of an optical registration algorithm when a surgical anchor member location is placed at different locations on the object of interest. For example, a surgical anchor member location that is placed at a more oblique angle relative to the camera 88 will appear to move a smaller distance in the viewing cone 89, thus lowering the accuracy of the optical registration compared to a case where the surgical anchor location is provided at a suitable position. Accordingly, the first and second sets of anchor member locations may be generated according to a criterion that are shared anchor member location also provides a stable optical registration. For each candidate surgical anchor member placement location, a measure of the potential optical registration accuracy can be derived (for example, using ray tracing approaches known in the art). Optical registration techniques are known to a person skilled in the art, and will not be repeated here (see the references cited in the definition section above).

Optionally, a mechanical stability constraint of the repositionable interventional platform is taken into account when performing the search for shared candidate surgical anchor member placement locations. It is important that the repositionable interventional platform does not move during an intervention, and a given configuration of support members 14a, 14b, 14c of a repositionable interventional platform might have better or worse mechanical stability (for example, tendency to move) for a specific choice of surgical anchor member locations at a given trajectory entry location.

The mechanical stability constraint data is, in an example, provided as a look-up table of experimentally obtained data defining, for a particular arrangement of support members 14a, 14b, 14c, how much deviation or flexure (in millimetres) of an experimental repositionable platform from a resting position occurs for particular arrangements of support members 14a, 14b, 14c. Alternatively or in addition, the mechanical stability constraint data may be provided as a mechanical model simulation of the interventional repositionable platform. Using such a look-up table or mechanical stability model is possible, for a set of candidate surgical anchor member placement locations, to evaluate for each of the set, a reaction of the repositionable interventional platform to a deviation caused by, for example, the insertion of a sEEG electrode into a medical tool support of the repositionable interventional platform. The candidate surgical anchor member placement locations are ranked based on their stability performance, and shared surgical anchor member placement locations are selected based upon having better stability performance (in other words, a set of surgical anchor member placement locations causing the repositionable interventional platform to deviate less from the trajectory entry point for an applied deviation force). Thus, the mechanical stability criterion is a threshold defining tolerable and intolerable mechanical deviations of the repositionable interventional platform relative to trajectory entry points.

Optionally, fixation orientation data of an object of interest may be provided. The provision of shared surgical anchor member placement locations may be made easier if the head of the patient (for example) is oriented in a specific manner. Accordingly, once a shared surgical anchor member location has been discovered, a head fixation vector may be generated to provide an optimal orientation of the object of interest. For example, the fixation orientation data of the object of interest could be provided so as to improve the resolution an optical registration system.

Figure 8A:
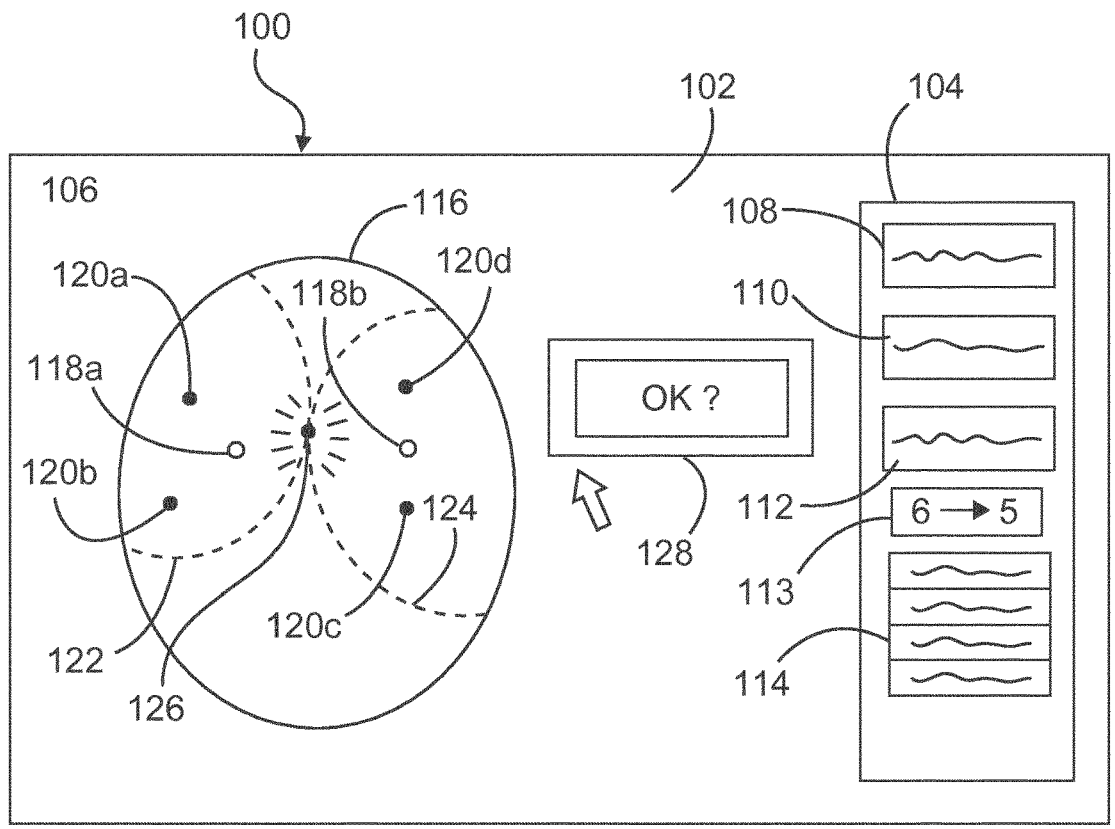
FIG. 8a) illustrates a GUI for reporting the position of a candidate shared anchor member location.

FIG. 8a) schematically illustrates a first example of a graphical user interface (GUI) 100 can be displayed on screen of an interventional system. The GUI comprises a workspace 102 having a sidebar 104 and a display region 106. The sidebar 104 provides tools for loading anatomical geometry data 108, surgical plan data 110, and geometric constraint data 112. Optionally, the GUI may provide more detailed configuration settings to configure the search algorithm, for example drop-down menu 114 enables a selection between a spherical algorithm and other search algorithms. The anatomical geometry data is displayed in the display region 106. A representation of an object of interest 116 derived from the anatomical geometry data and incorporating a first trajectory entry location 118a and a second trajectory entry location 118b. Candidate surgical anchor member placement locations 120a, 120b, 120c, and 120d represent fixed mounting points for a repositionable interventional platform in its first and second positions. The search algorithm (in this case a spherical search algorithm) has identified an intersection on the anatomical geometry data 116 between two expanding spheres 122 and 124 (the diagram illustrates contours of the intersection of the spheres with the object of interest for clarity). The GUI has identified via the computer implemented method according the first aspect that a candidate surgical anchor member placement location 126 could be shared between first and second interventions. This may optionally be indicated to the user of the GUI with a "blinking indicator". Optionally, the use of the GUI is prompted to agree to the positioning of the surgical anchor member placement location 126 as a shared surgical anchor member placement location by pop-up box 128. Accordingly, the GUI may optionally report the results of a fully automatic surgical anchor member location search to a user and ask for approval. Box 113 displays the reduction in the number of surgical anchor members possible according to the current version of the plan. Optionally, the geometric extent of the repositionable platform at each trajectory entry point is displayed on the GUI. Optionally, the user may "pick and place" surgical anchor members, and/or trajectory entry locations, and a live update may be calculated and displayed on the GUI.

Figure 8B:
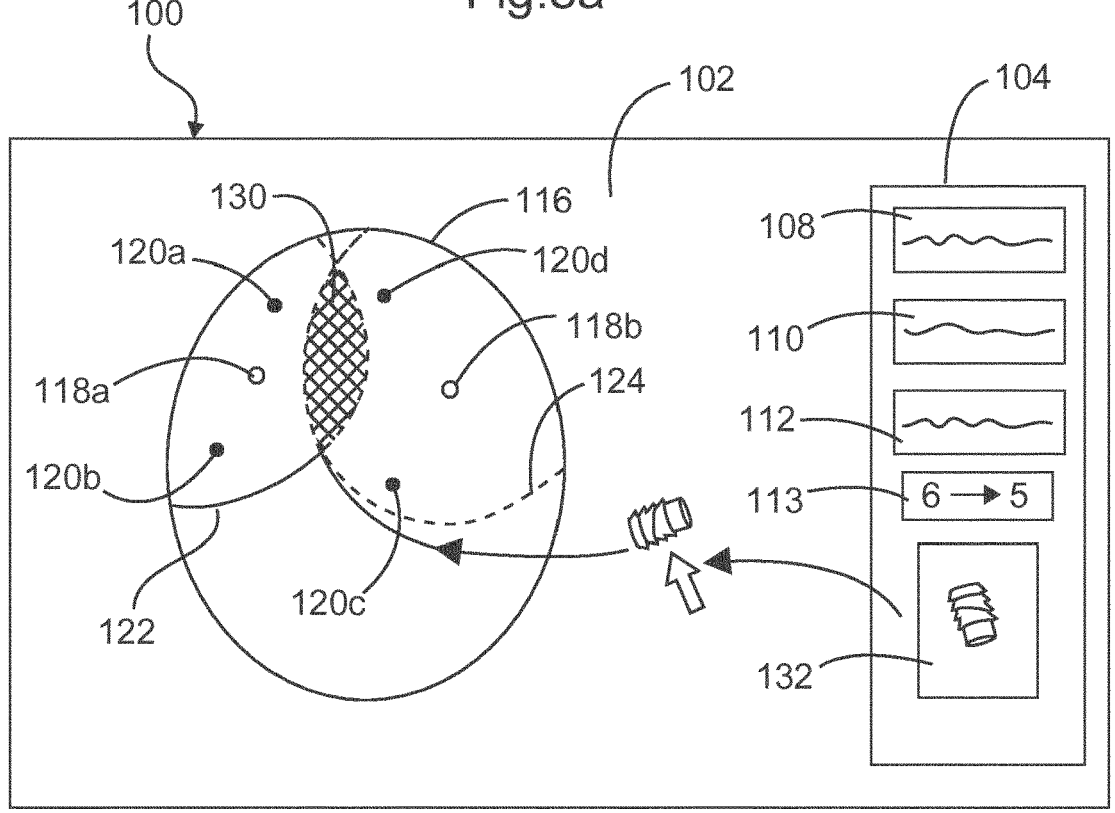
FIG. 8b) illustrates a GUI for user-driven placement of a candidate shared location within a proposed placement area.

FIG. 8b) schematically illustrates a second example of a surgical anchor placement GUI. Common aspects between the GUI of FIG. 8a) share the same labelling and are not described. In the second example, the two search regions have been allowed to extend their maximum extent, generating an intersecting region 130. As described above, a surgical anchor member placed anywhere inside the intersecting region 130 may be used as a shared surgical anchor member location. Accordingly, a user may pick a surgical anchor member type 132 from the toolbar 104, and "click and drag" the surgical anchor member across the GUI and place it anywhere within the intersecting region 130. This affords a medical professional some control over the placement of the shared surgical anchor member locations, whilst still enabling an overall reduction in the number of surgical anchors used.

Optionally, the GUI may display feedback of the optical fidelity and/or the mechanical stability of a repositionable interventional platform when positioned at each trajectory entry location.

Although to examples of a graphical user interface have been discussed, a skilled person will realise that many variations of a graphical user interface could be provided that make use of the computer implemented method according to the first aspect or any of its embodiments.

Optionally, the placement location data is generated to optimise a reduction in the number of surgical anchor members required to perform an intervention at the first and second trajectories. However, optimising the reduction in the number of surgical anchor members is not essential, because a reduction of only one surgical anchor member compared to a position where the computer incremented method according to the first aspect was not applied still has beneficial outcomes in terms of the number of surgical anchor members used and the inconvenience experienced by the patient.

Figure 9:
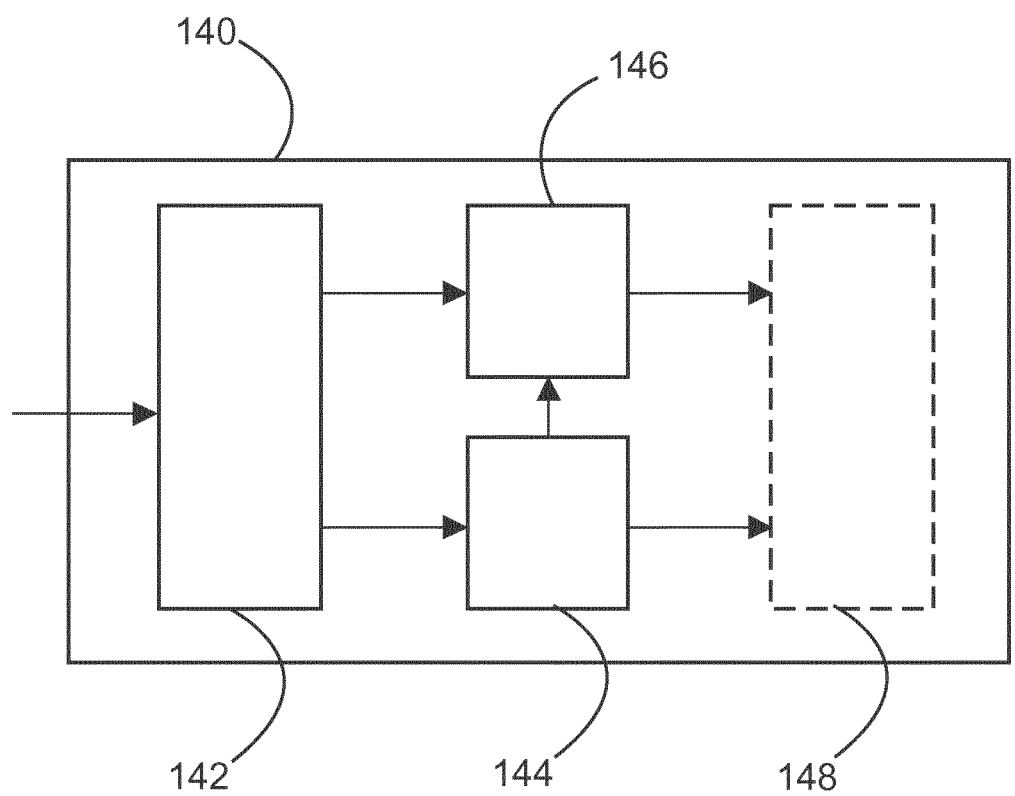
FIG. 9 schematically illustrates an apparatus according to the second aspect.

FIG. 9 schematically illustrates an apparatus according to the second aspect.

According to a second aspect, there is provided an apparatus 140 for generating placement location data for surgical anchor members. The apparatus comprises an input unit 142, a memory unit 144, and a processing unit 146. The apparatus 140 may be implemented, for example, as a personal computer (PC), a server, and the like. The input unit may comprise a data interface such as a Ethernet connection, a WiFi (TM) connection, a USB (TM), PACS, or FireWire connection, a connection to a hard disk or tape drive. A wide range of devices capable of supplying anatomical geometry data, surgical plan data, and geometric constraint data may be provided. The input device may be connected directly to a CT or MRI scanner to provide the anatomical geometry data, for example. Surgical plan data may be acquired from a data storage unit, or may optionally be acquired from a user interface (such the graphical user interface) of the apparatus or another computing apparatus used for planning an intervention. Likewise, the geometric constraint data of a repositionable interventional platform may be provided via a graphical user interface by a system user, but equally can be obtained from a server or computer memory having records of geometric constraint data of a repositionable interventional platform. Optionally, the input unit comprises a keyboard, mouse, touchscreen input, or another form of interface enabling a medical professional to interact with a graphical user interface and to control the apparatus 140.

The memory unit 144 may comprise, for example, a hard disk drive and/or random access memory, as considered appropriate for the stage of processing. For example, a large portion of anatomical geometry data may be stored in a hard disk drive. Short-term calculation data that is used during the process of generating placement location data according to the execution of the search algorithm may, for example, be stored in the random access memory. The memory unit 144 is configured to store program code configured to implement the computer-implemented method of the first aspect was optional embodiments.

The processing unit 146 may, for example, be a commodity processor such as an Intel™ i5, i7, or Xeon, or alternatively an AMD (TM) processor. Optionally, the processing unit 146 may be accelerated using a Graphics Processing Unit (GPU) for very computationally intensive tasks.

According to an embodiment, the apparatus 140 is provided with an output unit 148. This optionally comprises a graphics adapter to display, for example, a graphical user interface. Alternatively, the placement location data may be read from the memory unit 144 and communicated to an external server, an external client, and the like.

According to an aspect, there is provided the use of placement location data generated according to the program of claim 14 for the surgical treatment of a patient, comprising:

providing at least a first set and a second set of surgical anchor members at surgical anchor member placement locations defined in the placement location data on an object of interest, wherein at least one shared anchor member location that the repositionable interventional platform is anchored to during a first intervention along the first intervention trajectory and during a second intervention along the second intervention trajectory is present;

attaching a repositionable interventional platform to the first set of surgical anchor members;

performing an intervention into the object of interest along a first trajectory using the repositionable interventional platform;

reattaching a repositionable interventional platform from the first set to the second set of surgical anchor members;

performing a second intervention into the object of interest along a second trajectory using the repositionable interventional platform.

The following discusses further implementations and examples of the concept of the present invention, and this subject-matter is combinable with the embodiments discussed above. According to a first example of the use of the invention, in a first step a trajectory plan is loaded into the system. In second step, a search pattern having an increasing extent (such as a radius) identifies intersection points between trajectory entries in the trajectory plan that lie, for example, midway between the entries while satisfying avoidance criteria (for example, surgical anchor should not be placed near the sinuses, the eyes, or on the orbita, avoiding the ears and the hearing canal). The radius increase can optionally be performed at a homogenous velocity. Optionally, the radius increase can performed with a different velocity each trajectory according to the required accuracy criteria (dependent upon the anatomical region, for example from an anatomical atlas as brackets). Optionally, the velocity of the radius increase in search algorithm is a function of the decreasing navigation accuracy of the tracking system over time. The maximum search radius is a function of the physical extent of the landing platform (of a fixed robot) or the maximum extent of a interventional robot (walking spider leg). Optionally, instead of intersection points, intersection regions are also possible. Within the intersection regions, secondary criteria can be applied for screw placement (such as avoidance zones from an anatomical atlas, existing trajectories, or line of site optimisation).

Optionally, intersection points of the search pattern (determined surgical anchor locations) are ranked according to the number of trajectories that they can be used with. In other words, an intersection point that enables a greater saving of surgical anchor locations is ranked higher than an intersection point that enables a smaller saving of surgical anchor locations.

Optionally, additionally to the re-used points (shared surgical anchor members) entry-near points are determined (for example, having a fixed radius) for additional surgical anchor placement, if optical reregistration is planned for each trajectory one line-of-sight optimised bone screw is added to mount the reference array on later and marked as a navigation base. Line of site optimisation may be performed, for example, using a "lighthouse" approach on the trajectory (at an angle, for example, of 90°, or dependent on the type of marker device used).

On the basis of this plan, a head-fixation is recommended (such as a certain angle in a head clamp, a certain angle of a pneumatic fixator, a certain angle in a stereotactic head frame).

Subsequently, using optical navigation and a navigated (optically registered) screw drill, the surgical anchor members are placed.

If each trajectory is to be reregistered, the (optical) reference array is placed on the first trajectory navigation base, and the patient is reregistered using the other surgical anchor or bone anchor points.

The intervention device (walking spider, repositionable interventional platform) is now fixed to the surgical anchor members if they are also used for mechanical purposes and not only registration. At this point, an intervention into the relevant trajectory is performed. Following this, the trajectories may optionally be reregistered, following which the support members of the intervention device are moved on to a new set of surgical anchor members. Optionally, one of the surgical anchor members has been shared from one of the previous or future trajectory positions.

If the intervention device is to be used it can through robotic arm encoding or fixation of an optical array to the spider body in combination with angle and length information of the landing legs be affixed to all necessary surgical anchor members around an entry and moved around. The generated information is sufficient to perform registration. In a second step, the intervention device positions itself in order to execute the trajectory optimally.

Optionally, the entire process can be displayed and supported using an augmented reality device, where the user has better visualisation and better interaction (for example for fine placement of the screws).

Following this approach, it is possible to achieve heightened mechanical stability of intervention execution, increased accuracy, and minimisation of the number of invasive cranial screws the need to be placed into a patient.

Optionally, when the intervention device is provided as a repositionable intervention device capable of being moved between the surgical anchor members either automatically or with intervention of a medical professional (as a walking spider robot), panels attached to the intervention device may display various stages of moving the intervention robot body around with an optical reference array attached.

The walking spider can enter a mode where the spider body (the trajectory it can theoretically execute) is tracked, either by attaching an optical reference array or by being the active hand part of a robotic arm encoder tracked robotic arm. In this mode, the "legs" go limp. The feet are then attached to the bone screws or surgical anchor members (more than once a time-as many times a spider has legs). The bone screws have obviously been scanned prior to this registration process as in a FHC workflow.

When the interventional robot's body is now softly moved in circles (either passively, or potentially even actively moving), angle sensors at the feet of the interventional robot as well as links sensors in the legs of the interventional robot, it is possible to achieve a highly accurate spatial registration-essentially like using three or more pivot-based registration pointers at the same time. When registration is complete, the spider can switch into an active mode where the legs become rigid or actively controlled and finally navigate the spider body into the desired position so the plan trajectory can be perfectly executed.

Figure 10:
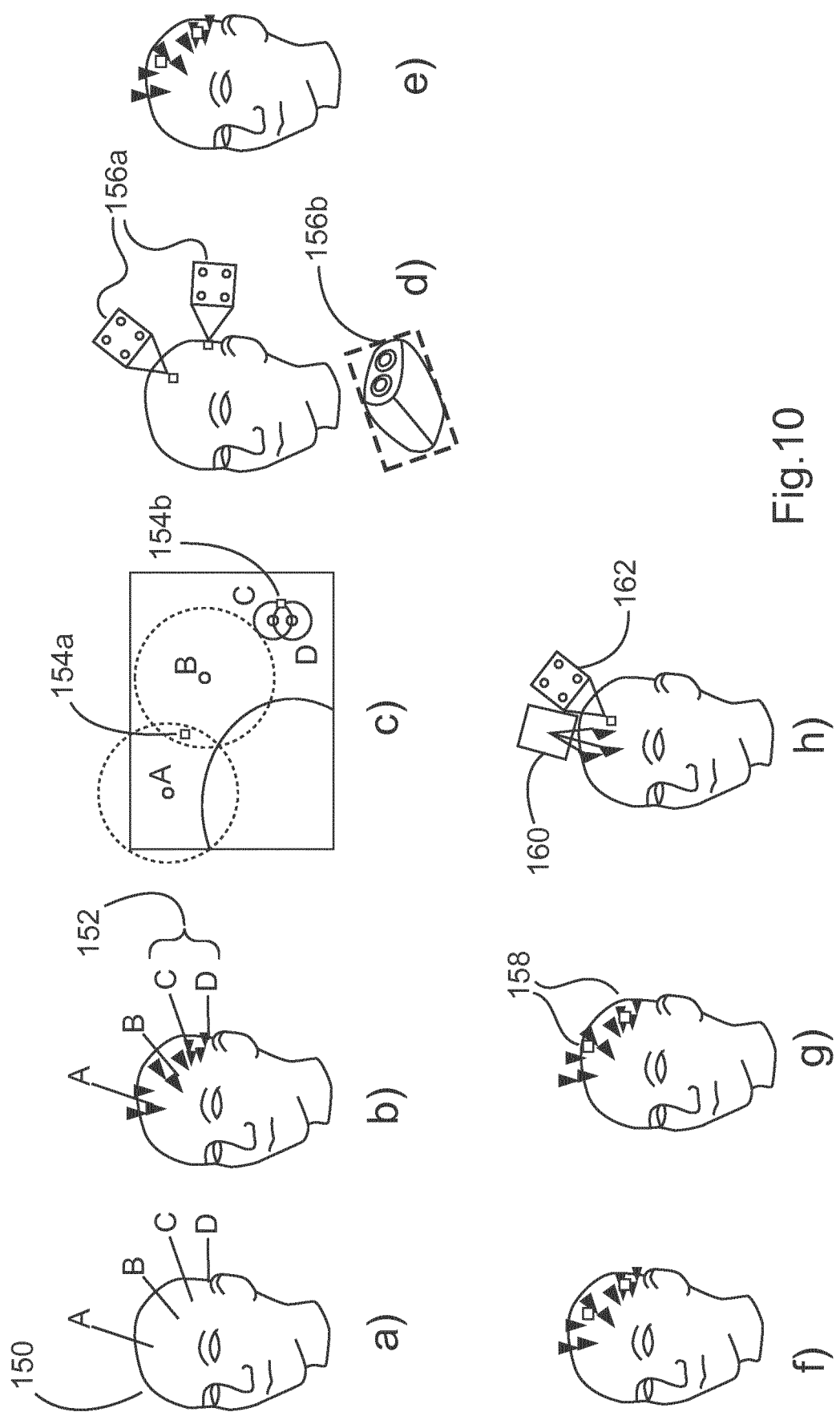
FIG. 10 schematically illustrates a use of the computer-implemented method in a medical workflow according to an example.

FIG. 10 schematically illustrates an example of a use of the computer-implemented method in a medical workflow according to an example.

At step a) of the use of the computer-implemented method according to FIG. 10, trajectories (in this example, four trajectories A, B, C, and D) are planned to enter the head of a patient 150.

At step b), the computer-implemented method and/or apparatus according to the first and/or second aspects are used to plan the location of surgical anchor members-in this case at least three being perpendicular to the skull, with a defined radius around the trajectory entry points. Notably, trajectories C and D 152 may be shared owing to their proximity.

At step c), surgical anchor member locations for near reference are identified. Thus locations 154a and 154b may be shared, respectively, between trajectories (A,B) and (C,D).

At step d), the permitted camera angles and distances of an optical registration system comprising optical reference markers 156a and a camera system 156b, and the recommended head fixation (such as the angle and/or inclination information of the head) are calculated.

At step e), the medical professional places optical navigation markers on the surface for registration purposes.

At step f), a scan to obtain further anatomical geometry data is performed, for example, using a CT scanner.

At step g), the surgical plan is updated with the real bone screw positions 158 after they have been placed.

At step h), a repositionable interventional platform 160 is placed on the surgical anchor members, along with an optical registration index 162. The surgical anchor members are reregistered at each location through the lander and the trajectory intervention is executed.

The invention claimed is:

1. A computer-implemented method for generating placement location data for surgical anchor members comprising:
   acquiring anatomical geometry data comprising a surface geometry of an object of interest;
   acquiring surgical plan data comprising at least first and second intervention trajectories into the object of interest relative to the anatomical geometry data;
   acquiring geometric constraint data of a repositionable interventional platform for supporting a surgical instrument on the object of interest along the first and second intervention trajectories; and
   generating placement location data for surgical anchor members comprising a first set of surgical anchor member placement locations for positioning the repositionable interventional platform on the object of interest at a location of the first intervention trajectory, and comprising a second set of surgical anchor member placement locations for positioning the repositionable interventional platform on the object of interest at a location of the second intervention trajectory;
   wherein the first set of surgical anchor member placement location data and the second set of surgical anchor member placement location data are generated according to a criterion that at least one shared anchor member location that the repositionable interventional platform is anchored to during a first intervention along the first intervention trajectory and during a second intervention along the second intervention trajectory is present.

2. The computer-implemented method according to claim 1, wherein generating the placement location data further comprises:
   generating a first plurality of candidate surgical anchor member placement locations in a first search region on a surface of the anatomical geometry data centered at the location of the first intervention trajectory;
   wherein the first search region has an extent defined by the geometric constraint data enclosing the location of the first intervention trajectory;
   generating a second plurality of candidate surgical anchor member placement locations in a second search region on a surface of the anatomical geometry data centered at the location of the second intervention trajectory;
   wherein the second search region has an extent defined by the geometric constraint data enclosing the location of the second intervention trajectory;
   generating a final candidate surgical anchor member placement location comprising candidate surgical anchor member placement locations inside an intersecting region of the first search region and the second search region.

3. The computer-implemented method according to claim 2, wherein generating the first search region and the second search region comprises:
   generating a first search region at the location of the first intervention trajectory having a first extent;
   generating a second search region at the location of the second intervention trajectory having a second extent;
   enlarging the first extent of the first search region and second extent of the second search region if an intersecting region of the first and second search regions is not found.

4. The computer-implemented method according to claim 2, wherein generating the first search region and the second search region comprises:
   enlarging the extent of the first search region at a greater rate than a rate of enlargement the extent of the second search region.

5. The computer-implemented method according to claim 2, wherein generating the final candidate surgical anchor member placement location inside the intersecting region is performed on the basis of an additional or alternative search criterion.

6. The computer-implemented method according to claim 2, further comprising:
   acquiring anatomical constraint data defining regions of an object of interest within which a surgical anchor should not be placed, and wherein generating the first search region and the second search region comprises:
   generating the first search region and the second search region on portions of the object of interest that do not intersect with the anatomical constraint data and/or providing first and second sets of anchor member locations that are not within the anatomical constraint data.

7. The computer-implemented method according to claim 2, further comprising:
   acquiring optical system constraint data defining the position of at least one camera relative to the anatomical geometry data, and wherein generating the first search region and the second search region comprises:
   generating, for each of the at least one shared anchor member locations an optical fidelity measure;

providing the first set and the second set of anchor member locations as locations meeting or exceeding an optical fidelity criterion.

8. The computer-implemented method according to claim 2, further comprising:
acquiring mechanical stability constraint data of the repositionable interventional platform and wherein generating the first search region and the second search region comprises:
generating, for each of the at least one shared anchor member locations, a mechanical stability measure;
providing the first and second sets of anchor member locations as locations meeting or exceeding a mechanical stability criterion.

9. The computer-implemented method according to claim 1, further comprising:
generating fixation orientation data of the object of interest based upon the placement location data.

10. The computer-implemented method according to claim 1, further comprising:
receiving, via a graphical user interface, a user selection of a preferred candidate surgical anchor member placement location of the shared candidate surgical anchor member placement locations;
generating updated positions of the surgical anchor member placement locations; and
displaying, via the graphical user interface, the updated positions of the surgical anchor member placement locations.

11. The computer-implemented method according to claim 1,
wherein the placement location data is generated to optimize a reduction in the number of surgical anchor members required to perform an intervention at the first and second trajectories.

12. The computer-implemented method according to claim 1, further comprising:
providing at least a first set and a second set of surgical anchor members at surgical anchor member placement locations defined in the placement location data on an object of interest, wherein at least one shared anchor member location that the repositionable interventional platform is anchored to during a first intervention along the first intervention trajectory and during a second intervention along the second intervention trajectory is present;
attaching a repositionable interventional platform to the first set of surgical anchor members;
performing an intervention into the object of interest along a first trajectory using the repositionable interventional platform;
reattaching a repositionable interventional platform from the first set to the second set of surgical anchor members;
performing a second intervention into the object of interest along a second trajectory using the repositionable interventional platform.

* * * * *